United States Patent [19]

Forman et al.

[11] Patent Number: 5,585,383
[45] Date of Patent: Dec. 17, 1996

[54] PROCESS FOR CRYSTALLIZING A 4-AZASTEROID 5ALPHA-REDUCTASE INHIBITOR

[75] Inventors: Andrew L. Forman, Scotch Plains; Sean R. Holihan, Dayton; Guy R. Humphrey, Belle Mead; David M. Lashen, Edison; James A. McCauley, Belle Mead, all of N.J.; Paul F. McKenzie, Yardley, Pa.; Ross A. Miller, Fanwood, N.J.; Pascal H. Toma, Piscataway, N.J.

[73] Assignee: Merck & Co., Inc., Rahway, N.J.

[21] Appl. No.: 434,082

[22] Filed: May 3, 1995

[51] Int. Cl.$^6$ .............................. C07S 73/00; A61K 31/58
[52] U.S. Cl. ................................. 514/284; 546/77
[58] Field of Search ................................ 546/77; 514/284

[56] References Cited

U.S. PATENT DOCUMENTS 5,237,064  8/1993  Bakshi et al. ............................. 546/77

FOREIGN PATENT DOCUMENTS

WO93/23419  11/1993  WIPO .
WO94/11387  5/1994  WIPO ..................................... 546/77

OTHER PUBLICATIONS

Helliker, Wall St. Jour. Jun. 7, 1991 pp. A1, A7.
Diani et al. Jour. Clin. Endocrin & METAB. vol. 74, No. 2, pp. 345–350 (1992).
Dunitz et al., "Disappearing Polymorphs", Accounts of Chem. Research, vol. 28, pp. 193–200 (1995).
McCauley, "Detection and Characterization of Polymorphism in the Pharmaceutical Industry", AIChE Symposium Series, Particle Design via Crystallizations, vol. 87, pp. 58–63 (1991).
McKenzie et al., "Mixing Induced Crystallization of an Aza Steroid", presented at the Engineering Foundation, Control of Particulate Processes Meeting, Alberta, Canada, May 17, 1995.
Bakshi et al, "7Beta–methyl–4–aza–cholestan–3–one (MK–386) and Related 4–Azasteroids as Selective Inhibitors of Human Type 1 5alpha–Reductase," J. Med. Chem., vol. 37, pp. 3871–3874 (1994).
Tolman et al., "4–Azasteroids as 5alpha–reductase inhibitors: Identification of 4,7beta–Dimethyl–4–aza–5alpha–cholestan–3–one (MK–386) As a Scalp Isozyme Selective Inhibitor", Proceedings of the European Medical Symposium (1994).

(List continued on next page.)

Primary Examiner—Donald G. Daus
Attorney, Agent, or Firm—Catherine D. Fitch; Melvin Winokur

[57] ABSTRACT

By this invention, there is provided a process for producing crystalline 4,7β-dimethyl-4-aza-5α-cholestan-3-one of structural formula (I) from 4,7β-dimethyl-4-aza-5α-cholestan-3-one oil.

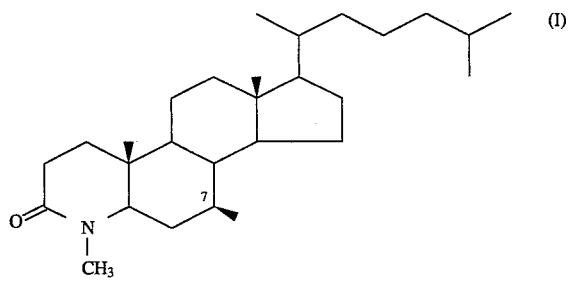

This crystallization process of the present invention comprises crystallization of the oil optionally containing residual solvent with vigorous but controlled agitation. Preferably, this crystallization process is carried out at select and controlled temperatures. Further, 4,7β-dimethyl-4-aza-5α-cholestan-3-one has been found to exist in at least two novel polymorphic nonsolvated forms, herein referred to as Form I and Form II. Form I can be prepared pure by careful control of the crystallization process.

23 Claims, 4 Drawing Sheets

OTHER PUBLICATIONS

Schwartz et al., "Pharmacodynamics of MK-386: A Novel Inhibitor of 5alpha-Reductase Type 1", Abstract in American Society for Clinical Pharmacology and Therapeutics, vol. 57, p. 171 (1995).

List Discotherm B–Product Specification Brochure (1991).

List Discotherm–Product Specification Brochure (1994).

List CRP–Product Specification Brochure (1994).

List–Equipment and Operation Units for Thermal Processes with Highly Viscous, Crusting & Free Flowing Products–Brochure (1994).

Myerson et al., "Crystals, Crystal Growth and Nucleation" in Handbook of Industrial Crystallization, Butterworth-Heineman (1993), pp. 33–63.

PROCESS FOR CRYSTALLIZING A 4-AZASTEROID 5ALPHA-REDUCTASE INHIBITOR

BACKGROUND OF THE INVENTION

Crystallization is typically viewed as a two step process: nucleation, or "birth" of new crystals, followed by crystal growth (Review—Myerson, A. S. 1993. Handbook of industrial crystallization. Butterworth-Heinemann. 43–52). Nucleation can be classified in two categories: primary and secondary. In primary nucleation, no seed crystals are present; whereas in secondary nucleation, presence of crystal surfaces has a catalyzing effect on the nucleation process.

Primary nucleation can be further subdivided as either homogeneous or heterogeneous. In homogeneous nucleation, the liquid is assumed to be free of any crystals or foreign particles, a situation rarely achieved. Due to fluctuations in local concentrations, ordered microregions appear. When these ordered clusters reach a critical size, nucleation occurs. In heterogeneous nucleation, foreign particles present in the bulk promote nucleation by reducing the energy required.

Despite years of research in the area of secondary nucleation, its mechanism and kinetics are still poorly understood. There are six proposed mechanisms: initial breeding, dendritic breeding, polycrystalline breeding, attrition breeding, contact nucleation, and fluid shear.

Initial breeding theory suggests that tiny crystallites that originate from the seed crystals behave as the nucleation sites. According to dendritic (needle) breeding theory, needle-like crystals form at high supersaturation levels. When they fragment, they serve as nucleation sites. At even higher supersaturation levels, formation and fragmentation of polycrystals provide the nucleation sites. Attrition breeding occurs at high stirring speeds, and involves macroabrasion of crystals; whereas contact nucleation involves microabrasion.

The theory of fluid shear nucleation suggests that a semi-ordered boundary layer present at an interface (crystal/bulk solution, crystal/melt, air/liquid, etc.) is scraped off into the bulk forming a semi-ordered cluster. As smaller clusters merge together and form larger ones, nucleation occurs when the critical size is achieved.

Crystallization by growth occurs when molecules adsorb to the surface of an existing crystal and order themselves to fit into the existing crystal structure, forming layers. As the layers accumulate, faces of the crystal begin to grow.

The compound 4,7β-dimethyl-4-aza-5α-cholestan-3-one of structural formula (I)

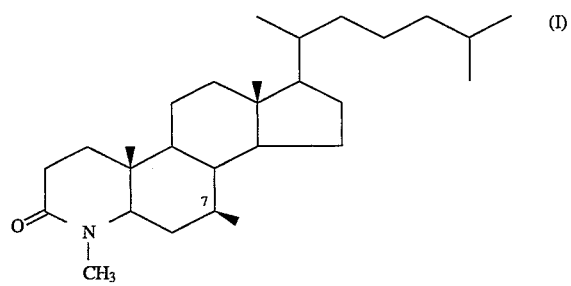

is an inhibitor of 5α-reductase type 1, useful in treating acne vulgaris, sweat disorders, seborrhea, androgenic alopecia (also called "androgenetic alopecia"), and benign prostatic hyperplasia. The compound 4,7β-dimethyl-4-aza-5α-cholestan-3-one is disclosed in PCT publication WO 93/23419. Briefly, 4,7β-dimethyl 4-aza-5α-cholestan-3-one oil is synthesized in a 9-step process starting with cholesteryl acetate. The final synthetic step in the process to manufacture 4,7β-dimethyl-4-aza-5α-cholestan-3-one results in an oil which does not respond to typical crystallization methods.

What is desired herein is a method for the crystallization of 4,7β-dimethyl-4-aza-5α-cholestan-3-one to produce the thermodynamically most stable crystalline polymorphic form of 4,7β-dimethyl-4-aza-5α-cholestan-3-one.

Polymorphism can be defined as the ability of the same chemical substance to exist in different molecular packing arrangements. The different structures are referred to as polymorphs, polymorphic modifications, or forms. From a pharmaceutical standpoint, it is desirable to form a product in an energetically stable crystalline form. From a manufacturing process standpoint, it is desirable to achieve this crystalline form using techniques that are fast, reproducible and predictable. Furthermore, these techniques, which are defined by the present invention as operating parameters, should be predictive of success at different production scales, from lab to pilot plant to manufacturing scale.

SUMMARY OF THE INVENTION

By this invention, there is provided a process for producing crystalline 4,7β-dimethyl-4-aza-5α-cholestan-3-one of structural formula (I) from 4,7β-dimethyl-4-aza-5α-cholestan-3-one oil.

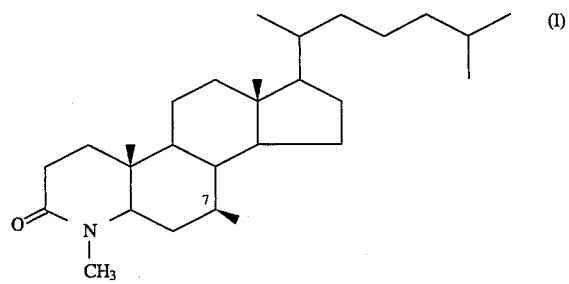

This crystallization process of the present invention comprises crystallization of the oil optionally containing residual solvent with vigorous but controlled agitation at a temperature less than 60° C. Preferably, this crystallization process is carded out at select and controlled temperatures. Further, 4,7β-dimethyl-4-aza-5α-cholestan-3-one has been found to exist in at least two novel polymorphic nonsolvated forms, herein referred to as Form I and Form II. Pure Form I polymorph can be prepared by careful control of the crystallization process. By pure, it is meant an HPLC weight percent of Form I crystals of greater than 98.5%, a maximum total HPLC area % of impurities of 1.5 area %, no single impurity greater than 0.5 area percent, residual solvents less than 0.3 weight % of total, KF (residual water) less than 1.0% and Heavy metals less than or equal to 10 ppm. The meta stable Form II transforms to Form I with time and/or mechanical manipulation.

DETAILED DESCRIPTION OF THE INVENTION

Figure 1:
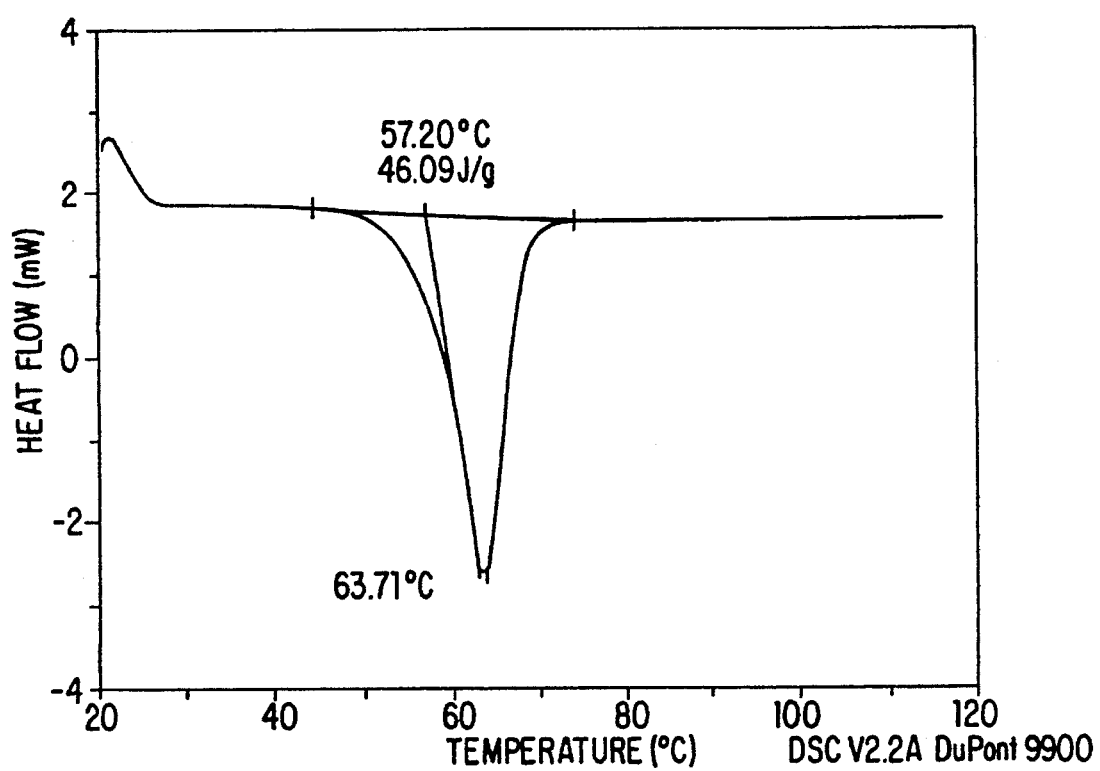
FIG. 1: depicts the differential scanning calorimetry plot of 4,7β-dimethyl-4-aza-5α-androstan-3-one crystals of polymorphic Form I.

The present invention provides for a method of crystallizing 4,7β-dimethyl-4-aza-5α-cholestan-3-one of structural formula I:

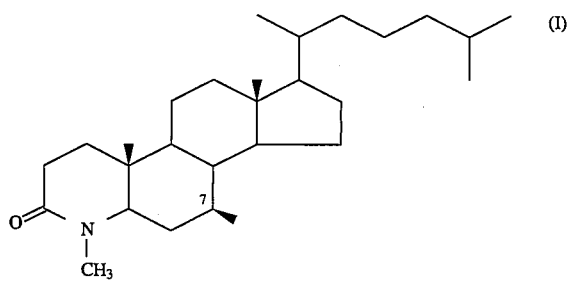

from 4,7β-dimethyl-4-aza-5α-cholestan-3-one oil optionally containing residual solvent, as well as crystalline polymorphic Form I and II of the compound of structural formula I.

The term "4,7β-dimethyl-4-aza-5α-cholestan-3-one oil" comprises not only the oil form of 4,7β-dimethyl-4-aza-5α-cholestan-3one, but also any amorphous or partially crystallized solid form of 4,7β-dimethyl-4-aza-5α-cholestan-3-one, such as glasses, lyophilizates, and mixtures thereof, which may be converted to 4,7β-dimethyl-4-aza-5α-cholestan-3-one oil through warming.

The present process involves extensive mixing of the oil, preferably under controlled temperature conditions, throughout the entire crystallization process. Optionally, the oil contains residual solvent. Since toluene is the solvent for the final synthetic step in making 4,7β-dimethyl-4-aza-5α-cholestan-3-one, the residual solvent is preferably toluene. Other suitable solvents include any other organic solvent for the oil such as heptane, tetrahydrofuran (THF), acetone, acetic acid, methanol and the like.

The residual solvent may be present from 0 to 10 wt %. Preferably residual solvent is present from 1 to 8 wt %. Most preferably, residual solvent is present at 5 wt %. The crystallization time (induction period and total time required to convert to Form I) is shorter when residual solvent is present. Residual solvent aids in both heat and mass transfer in the oil.

A crystallization profile can be broken down into two separate regions: the first where the rate of crystallization is about zero, and the second where the rate of crystallization is a maximum. The term "induction period" is used to refer to the first region of the crystallization profile, wherein the rate of crystallization is about zero.

Preferably, the 4,7β-dimethyl-4-aza-5α-cholestan-3-one oil is agitated at a high rate. With increasing agitation level, induction time decreases and the crystallization rate increases. More preferably, this agitation is macroscopic and/or microscopic. Most preferably, this agitation level is both macroscopic and microscopic. A high and continuous and extensive rate facilitates crystallization and reduces induction time.

Additionally, the 4,7β-dimethyl-4-aza-5α-cholestan-3-one oil may be seeded with 0 up to 100% by weight crystalline 4,7β-dimethyl-4-aza-5α-cholestan-3-one Form I, preferably 5 to 10 wt %, most preferably 10 wt %. The term "100% by weight crystalline 4,7β-dimethyl-4-aza-5α-cholestan-3-one Form I" means that if one is trying to crystallize 2 kg of 4,7β-dimethyl-4-aza-5α-cholestan-3-one oil, one would add 2 kg crystalline 4,7β-dimethyl-4-aza-5α-cholestan-3-one Form I seed. It is preferable to add the seed crystals with agitation to the oil that is held at a temperature below 55° C. The seed may be added at any time after the oil is cooled to below 55° C. The seed may be added with or without agitation. Preferably, the seed is added at the beginning of the agitation since this facilitates reduction of the induction time. It is preferable to not exceed a temperature of 55° C., which is approaching the melting point of Form I.

The crystallization process of the present invention may be carried out between −5° and 60° C. All temperatures in this range are desirable. The analytical profile (percent of formation and distribution of the crystalline polymorphs graphed over time) obtained during the crystallization will vary with temperature: Form II will be formed at temperatures below 40° C. and will convert to Form I with mixing. Form I will form between 40°–55° C., but will begin to melt at temperatures greater than 55° C. As crystalline 4,7β-dimethyl-4-aza-5α-cholestan-3-one Form I is the most desired for pharmaceutical purposes, most preferably, the crystallization operation is carried out at 40° to 45° C. Conducting crystallization at this temperature range prevents the formation of undesirable Form II crystals which could potentially occur at lower temperatures and eliminates the problem of melt-back of Form I crystals as the operation temperature approaches the Form I melt temperature, as discussed above.

The crystallization process of the present invention is advantageously conducted under an inert atmosphere, that is, an atmosphere not containing oxygen, such as nitrogen, helium and argon, preferably nitrogen. The inert atmosphere is used as a precaution to minimize any opportunity for thermal or oxidative decomposition.

The process of the present invention is most advantageously carried out with pure 4,7β-dimethyl-4-aza-5α-cholestan-3-one oil. By "pure", it is meant an area percent of greater than 99.0% for 4,7β-dimethyl-4-aza-5α-cholestan-3-one. Since this is the final step in a synthesis, oil with impurities present at a level greater than 3.5 area percent is not desirable. With impurities present, the crystallization will still proceed, but at a slower rate.

Addition of non-solvents does not appear to aid the process of the present invention and is not preferred. For example, the addition of 50% by weight deionized water to seeded 4,7β-dimethyl-4-aza-5α-cholestan-3-one oil prior to crystallization resulted in the formation of an emulsion and prevention of crystallization. However, water addition to samples achieving greater than 50% crystallinity has no real effect.

Similarly, addition of non-solvents plus additives does not appear to aid the process of the present invention and is not preferred. For example, the addition of water and surface active agents such as pluronic diblock copolymer of polyethylene glycol and polypropylene glycol to 4,7β-dimethyl-4-aza-5α-cholestan-3-one oil prior to crystallization resulted in an emulsion with no improvement in crystallization.

The crystallization experiments of the present invention were carded out in a List Discotherm B mixer manufactured by List, Inc. of Acton, Mass. However, any device capable of continuously, thoroughly, mixing the viscous subcooled melt in various stages of crystallinity and simultaneously providing temperature control and a means for adding seed is satisfactory. Preferably, the device permits both macroscopic and microscopic mixing. It is preferred that the device also provide a means for inerting the atmosphere. Specifically, the device should be capable of mixing a viscous material while maintaining batch temperature below 60° C. Examples of such devices include: single or twin screw extruders, blenders, kneaders and the like. The List Discotherm B mixer employed in the present invention is a kneader designed for highly viscous and crust-forming products. The main feature of the List Discotherm B Mixer is the high torque and thorough mixing and kneading action throughout the sample which takes place due to interaction between the transport bars on the agitator and the hook-shaped static counter paddles mounted on the cylindrical housing. The mixer employed had the following characteristics:

Total Casing Volume: 2.65 liters

Weight: approx. 145 kg

Speed Range of Shaft: 0 to 65 rpm

Torque: 161 Nm at 65 rpm

To provide temperature control, the mixer was jacketed. To provide an inert atmosphere, the mixer had sealed bearings and a port for positive nitrogen pressure.

Preferably, the mixer was run with about 1 kg of 4,7β-dimethyl-4-aza-5α-cholestan-3-one oil, which roughly corresponded to a fill volume of 50%. Use of less than a 50% fill volume resulted in the oil wrapping around the shaft, thereby sequestering it from the hooks on the housing, resulting in poor mixing. Use of a fill volume much greater than 50% put a strain on the motor as the oil crystallized, because it was undersized for the torque required to maintain the rpm during the crystallization process.

The crystallinity of each batch was determined primarily from Differential Scanning Calorimetry (DSC) employing a DuPont Model 910 Thermal Analyzer. However, any other reliable means may be employed to determine the crystallinity of a sample, such as x-ray powder diffraction, solid state NMR, or polarizing microscopy.

Generally, a DSC sample was prepared by weighing. 10 to 30 mg of material into a DSC cup and crimping the cup closed. Preferably, each DSC sample was run as soon as possible after preparation, most preferably within 15 minutes of preparation, because crystallinity increases with aging. Generally, samples were heated at a rate of 10° C./min from 10° C. to 100° C. under nitrogen. The DSC peaks were integrated and the measured heat of formation was divided by 46.6 J/g (the average heat of formation of samples confirmed by x-ray diffraction to contain no Form II) to calculate the percent crystallinity of the sample. The term percent crystallinity refers to the weight percent of 4,7β-dimethyl-4-aza-5α-cholestan-3-one sample weight in Form I.

X-ray diffraction was also employed to confirm DSC results. The diffraction patterns samples from a crystallization batch were compared with the known diffraction patterns of polymorph Form I and Form II to confirm the presence or absence of a crystal form. This method was not employed for quantitative analysis of the degree of crystallinity.

HPLC, high pressure liquid chromatography, and thermogravimetric analysis were used to determine the toluene content of the batches. HPLC was also used to monitor the presence of any impurities that might form through thermal or oxidative decomposition. HPLC samples were diluted in acetonitrile to a concentration of about 1 mg/mL. The following assay was used:

column: Zorbax™ Phenyl SB; 25 cm×4.6 mm ID packing size: 5 microns solvent: (A) $H_2O$ (0.1% $H_3PO_4$) (B) $CH_3CN$ gradient: isocratic, 17% $H_2O$ (0.1% $H_3PO_4$): 83% $CH_3CN$ flow: 1.8 mL/min.

wavelength: 210 nm detector: Specta System VV1000 by Spectra Physics

Column Temp.: 25° C.

Injection Volume: 10 mL

| Constituent | Retention Time (min.) |
|---|---|
| 4,7β-dimethyl-4-aza-5α-cholestan-3-one | 18.7 |
| Toluene | 1.9 |

The impurity profile did not change during the course of the experiments.

The Scanning Electron Microscope (SEM) may be employed to observe the crystallization process. The Electroscan 2010 manufactured by Electroscan, Wilmington, Mass., U.S.A., permitted observations at a magnification of up to 1750×. Samples were prepared by freezing the material in liquid nitrogen, breaking the frozen glass and mounting it on the observation stage using double-sided tape.

In its broadest sense, the present process comprises: agitating 4,7β-dimethyl-4-aza-cholestan-3-one oil to obtain crystalline material under controlled conditions, and recovering the crystalline material.

The product of the present process is crystalline polymorphic Form I which is a crumbly solid. The solid may be removed either with or without a water slurry, carrier or diluent. Any residual solvent may be removed by vacuum evaporation. This solid may advantageously be taken forward for size reduction via wet-milling and subsequently for further formulation into a pharmaceutical product. Wet milling is the process where a mixture of a crystalline product and water are agitated in a high-speed blender, such as a WARING blender. Wet milling reduces the particle size. Wet milling of the products of the present invention is preferably completed at a temperature below 60° C., preferably with cold water. Wet milling may be followed by filtration and drying before formulating a pharmaceutical product.

Thus, one class of the process of the present invention comprises:

agitating 4,7β-dimethyl-4-aza-5α-cholestan-3-one oil at a temperature less than 60° C., and recovering the crystalline 4,7β-dimethyl-4-aza-5α-cholestan-3-one.

A sub-class of the process of the present invention comprises:

agitating 4,7β-dimethyl-4-aza-5α-cholestan-3-one oil at a temperature less than 60° C. under an inert atmosphere, and recovering the crystalline 4,7β-dimethyl-4-aza-5α-cholestan-3-one.

A preferred embodiment of the sub-class of the process of the present invention comprises:

agitating 4,7β-dimethyl-4-aza-5α-cholestan-3-one oil at a temperature less than 60° C. under a nitrogen atmosphere, and recovering the crystalline 4,7β-dimethyl-4-aza-5α-cholestan-3-one.

An especially preferred embodiment of the sub-class of the process of the present invention comprises:

agitating 4,7β-dimethyl-4-aza-5α-cholestan-3-one oil at a temperature between 40° and 55 ° C. under a nitrogen atmosphere, and recovering the crystalline 4,7β-dimethyl-4-aza-5α-cholestan-3-one.

Still another subclass of the process of present invention comprises:

agitating 4,7β-dimethyl-4-aza-5α-cholestan-3-one oil containing residual solvent at a temperature less than 60° C. to obtain crystalline 4,7β-dimethyl-4-aza-5α-cholestan-3-one of polymorphic Form I, and recovering the crystalline 4,7β-dimethyl-4-aza-5α-cholestan-3-one Form I.

A preferred embodiment of this class of the invention comprises:

agitating 4,7β-dimethyl-4-aza-5α-cholestan-3-one oil containing residual solvent wherein the residual solvent is selected from heptane, tetrahydrofuran, acetone, acetic acid, methanol and toluene at a temperature less than 60° C., and recovering the crystalline 4,7β-dimethyl-4-aza-5α-cholestan-3-one.

An especially preferred embodiment of this class of the invention comprises:

agitating 4,7β-dimethyl-4-aza-5α-cholestan-3-one oil containing residual solvent wherein the residual solvent is toluene at a temperature less than 60° C., and recovering the crystalline 4,7β-dimethyl-4-aza-5α-cholestan-3-one.

Another especially preferred embodiment of this class of the invention comprises:

agitating 4,7β-dimethyl-4-aza-5α-cholestan-3-one oil containing residual solvent wherein the residual solvent is toluene at a temperature between 40° and 550C, and recovering the crystalline 4,7β-dimethyl-4-aza-5α-cholestan-3-one.

Yet another class of the process of the present invention comprises:

agitating 4,7β-dimethyl-4-aza-5α-cholestan-3-one oil at a temperature less than 60° C., seeding with crystalline 4,7β-dimethyl-4-aza-5α-cholestan-3-one, and recovering the crystalline 4,7β-dimethyl-4-aza-5α-cholestan-3-one.

A preferred embodiment of this class of the invention comprises:

agitating 4,7β-dimethyl-4-aza-5α-cholestan-3-one oil at a temperature less than 60° C., seeding with 1 to 100 weight percent crystalline 4,7β-dimethyl-4-aza-5α-cholestan-3-one Form I, and recovering the crystalline 4,7β-dimethyl-4-aza-5α-cholestan-3-one Form I.

An especially preferred embodiment of this class of the invention comprises:

agitating 4,7β-dimethyl-4-aza-5α-cholestan-3-one oil at a temperature less than 60° C., seeding with 5 to 10 weight percent crystalline 4,7β-dimethyl-4-aza-5α-cholestan-3-one Form I, and recovering the crystalline 4,7β-dimethyl-4-aza-5α-cholestan-3-one Form I.

A further preferred embodiment of this class of the invention comprises:

agitating 4,7β-dimethyl-4-aza-5α-cholestan-3-one oil at a temperature between 45° and 60° C., seeding with 5 to 10 weight percent crystalline 4,7β-dimethyl-4-aza-5α-cholestan-3-one Form I, and recovering the crystalline 4,7β-dimethyl-4-aza-5α-cholestan-3-one Form I.

An especially preferred embodiment of the invention comprises:

agitating 4,7β-dimethyl-4-aza-5α-cholestan-3-one oil containing residual solvent at a temperature less than 60° C., seeding with 10 weight percent crystalline 4,7β-dimethyl-4-aza-5α-cholestan-3-one Form I, and recovering the crystalline 4,7β-dimethyl-4-aza-5α-cholestan-3-one Form I.

A further preferred embodiment of the invention comprises:

agitating 4,7β-dimethyl-4-aza-5α-cholestan-3-one oil containing residual solvent at a temperature between 40° and 55° C., seeding with 10 weight percent crystalline 4,7β-dimethyl-4-aza-5α-cholestan-3-one, and recovering the crystalline 4,7β-dimethyl-4-aza-5α-cholestan-3-one Form I.

Yet another class of the process of the present invention comprises:

agitating 4,7β-dimethyl-4-aza-cholestan-3-one oil at a temperature less than 60° C. to obtain crystalline 4,7β-dimethyl-4-aza-cholestan-3-one of polymorphic Form I, wet milling the crystalline 4,7β-dimethyl-4-aza-cholestan-3-one of polymorphic Form I, and optionally formulating the milled crystalline 4,7β-dimethyl-4-aza-5α-cholestan-3-one of polymorphic Form I into a suitable pharmaceutical composition.

One subclass of this process of the present invention comprises:

agitating 4,7β-dimethyl-4-aza-cholestan-3-one oil at a temperature between 45° and 55° C. to obtain crystalline 4,7β-dimethyl-4-aza-cholestan-3-one of polymorphic Form I, wet milling the crystalline 4,7β-dimethyl-4-aza-cholestan-3-one of polymorphic Form I, and optionally formulating the milled crystalline 4,7β-dimethyl-4-aza-5α-cholestan-3-one of polymorphic Form I into a suitable pharmaceutical composition.

Crystalline 4,7β-dimethyl-4-aza-5α-cholestan-3-one has been found to exist in two non-solvated polymorphic forms, Form I and Form II, each of which may be selectively prepared.

Figure 2:
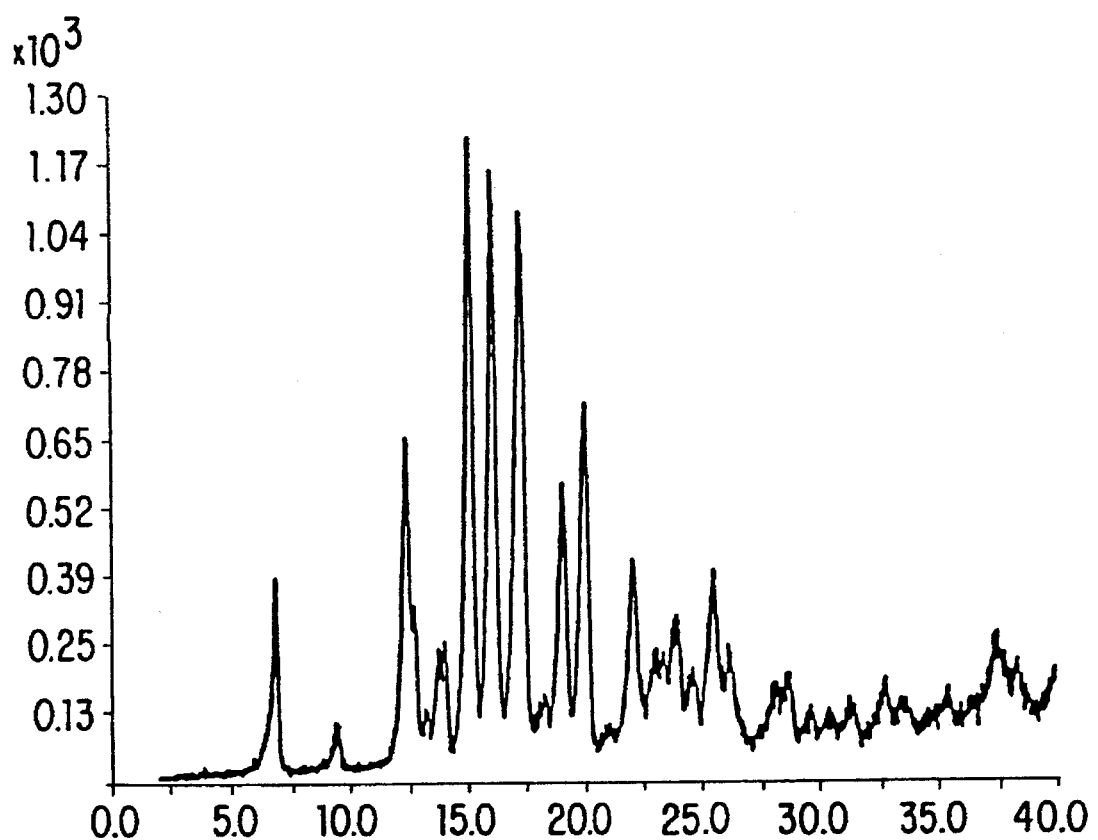
FIG. 2: depicts the x-ray powder diffraction pattern of polymorphic Form I crystals.

Form I is the more stable, energetically favored polymorph. Form I melts between 60° and 65° C. as determined by Differential Scanning Calorimetry (DSC), and as shown in FIG. 1. The x-ray powder diffraction pattern for Form I is shown in FIG. 2, and the peaks are listed below in Table 1.

TABLE 1

| | X-ray powder diffraction pattern — Form I crystals | | | | | | |
|---|---|---|---|---|---|---|---|
| Peak no. | Angle (deg.) | Tip width (deg.) | Peak intensity (cts.) | Background (cts.) | D spacing (Ang) | I/Imax (%) | Sign |
| 1 | 2.855 | 0.72 | 10 | 7 | 30.9209 | 0.98 | 1.10 |
| 2 | 6.970 | 0.10 | 335 | 16 | 12.6721 | 31.9 | 6.03 |
| 3 | 9.510 | 0.21 | 77 | 18 | 9.2925 | 7.38 | 3.72 |
| 4 | 12.430 | 0.09 | 576 | 20 | 7.1153 | 54.87 | 2.00 |
| 5 | 12.750 | 0.07 | 262 | 20 | 6.9374 | 25.00 | 0.79 |
| 6 | 13.183 | 0.15 | 102 | 22 | 6.7108 | 9.72 | 0.85 |
| 7 | 13.680 | 0.18 | 196 | 24 | 6.4678 | 18.67 | 1.86 |

TABLE 1-continued

X-ray powder diffraction pattern — Form I crystals

| Peak no. | Angle (deg.) | Tip width (deg.) | Peak intensity (cts.) | Back-ground (cts.) | D spacing (Ang) | I/Imax (%) | Sign |
|---|---|---|---|---|---|---|---|
| 8 | 14.045 | 0.13 | 199 | 24 | 6.3006 | 18.94 | 4.27 |
| 9 | 15.2 | 0.16 | 1050 | 29 | 5.8243 | 100.0 | 15.49 |
| 10 | 16.228 | 0.06 | 894 | 32 | 5.4577 | 85.16 | 0.87 |
| 11 | 17.075 | 0.15 | 605 | 35 | 5.1867 | 57.65 | 0.98 |
| 12 | 17.430 | 0.10 | 930 | 36 | 5.0838 | 88.62 | 5.37 |
| 13 | 18.283 | 0.15 | 108 | 40 | 4.8487 | 10.30 | 1.17 |
| 14 | 19.167 | 0.09 | 445 | 44 | 4.6267 | 42.41 | 1.78 |
| 15 | 20.140 | 0.15 | 543 | 46 | 4.4055 | 51.72 | 8.13 |
| 16 | 21.030 | 0.36 | 42 | 49 | 4.2210 | 4.02 | 0.91 |
| 17 | 22.300 | 0.09 | 339 | 53 | 3.9834 | 32.25 | 1.17 |
| 18 | 23.083 | 0.24 | 156 | 58 | 3.8501 | 14.88 | 0.78 |
| 19 | 24.153 | 0.12 | 216 | 61 | 3.6819 | 20.58 | 1.12 |
| 20 | 24.725 | 0.36 | 128 | 62 | 3.5983 | 12.16 | 3.89 |
| 21 | 25.613 | 0.36 | 303 | 66 | 3.4752 | 28.84 | 11.22 |
| 22 | 26.253 | 0.21 | 154 | 67 | 3.3919 | 14.65 | 1.93 |
| 23 | 28.225 | 0.30 | 98 | 66 | 3.1592 | 9.34 | 2.04 |
| 24 | 28.910 | 0.21 | 106 | 66 | 3.0859 | 10.11 | 1.82 |
| 25 | 29.823 | 0.15 | 40 | 79 | 2.9935 | 3.78 | 0.95 |
| 26 | 30.488 | 0.36 | 29 | 79 | 2.9297 | 2.78 | 0.76 |
| 27 | 31.465 | 0.42 | 38 | 86 | 2.8409 | 3.66 | 3.98 |
| 28 | 32.785 | 0.24 | 88 | 76 | 2.7295 | 8.42 | 1.62 |
| 29 | 33.495 | 0.30 | 56 | 61 | 2.6732 | 5.36 | 0.93 |
| 30 | 35.445 | 0.42 | 45 | 94 | 2.5305 | 4.28 | 2.57 |
| 31 | 36.325 | 0.42 | 45 | 94 | 2.5305 | 4.28 | 2.57 |
| 32 | 37.435 | 0.42 | 132 | 104 | 2.4004 | 12.6 | 4.07 |
| 33 | 36.398 | 0.09 | 92 | 112 | 2.3424 | 9.34 | 0.78 |

Figure 3:
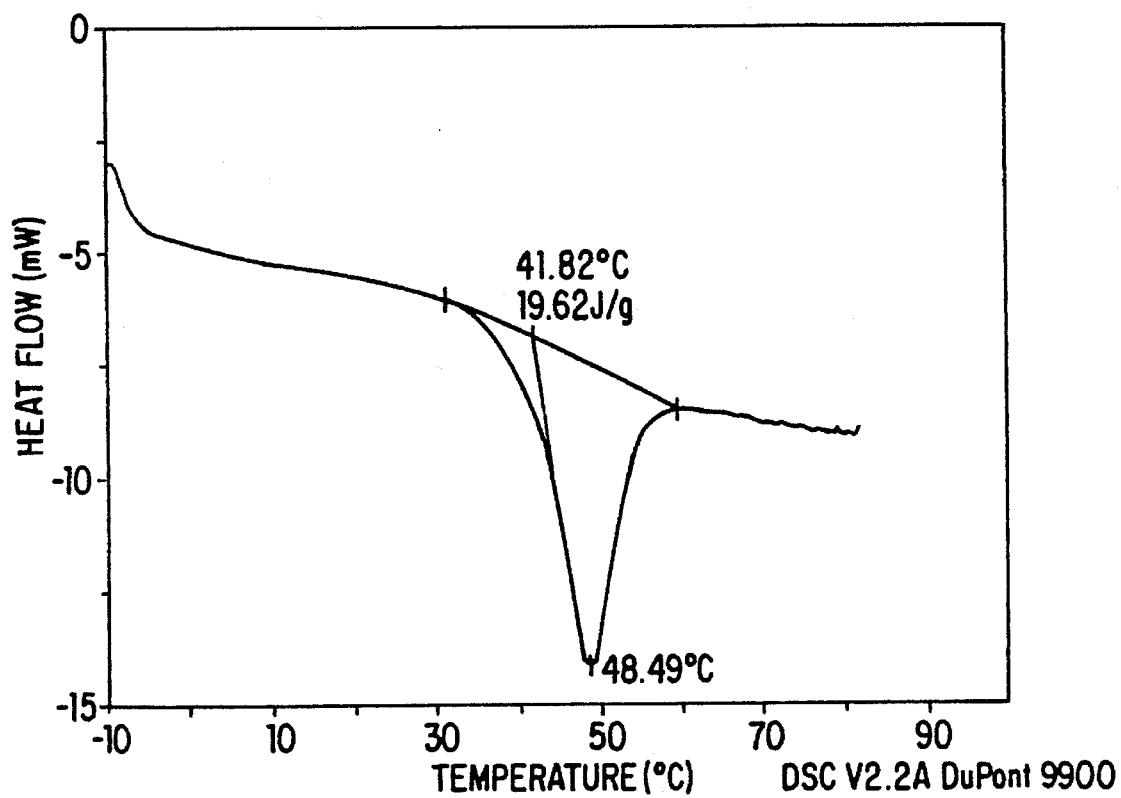
FIG. 3: depicts the differential scanning calorimetry plot of 4,7β-dimethyl-4-aza-5α-androstan-3-one crystals of polymorphic Form II.
Figure 4:
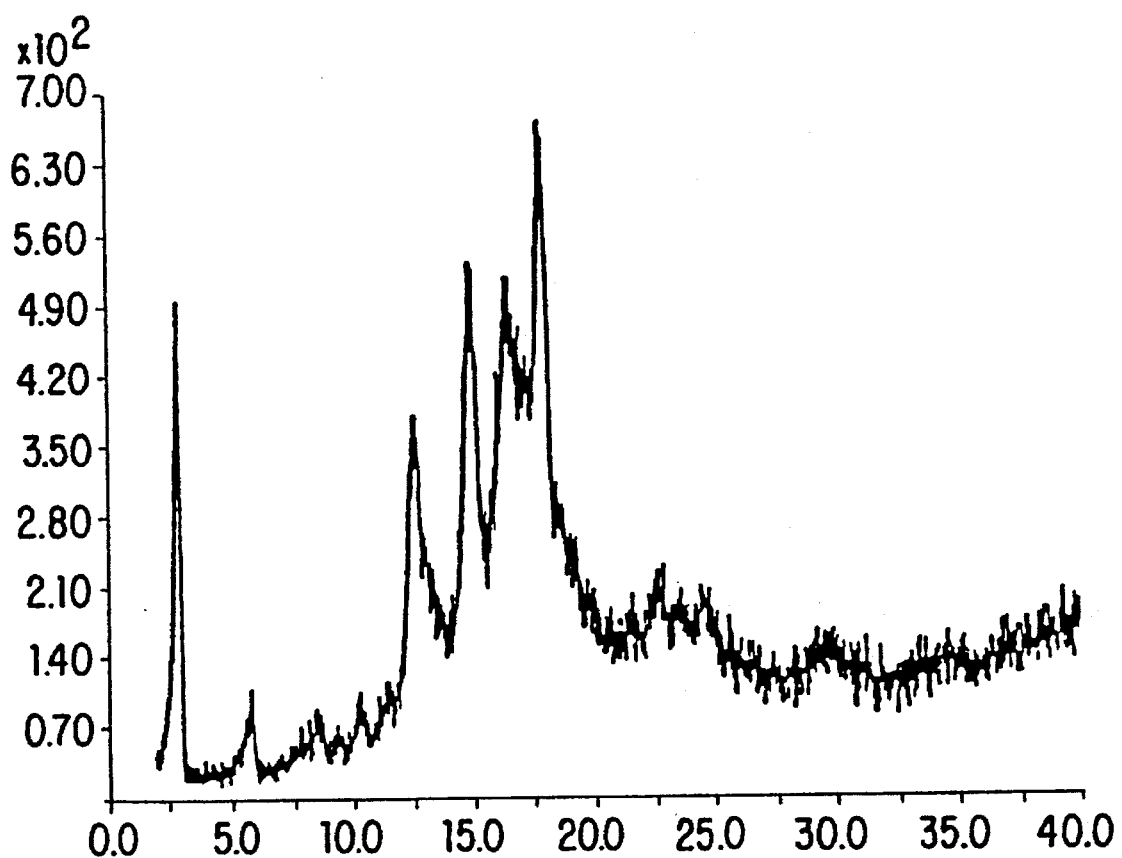
FIG. 4: depicts the x-ray powder diffraction pattern of polymorphic Form II crystals.

Form II is the less energetically favored polymorph and melts at approximately 40° C., as determined by DSC and shown in FIG. 3. The x-ray powder diffraction pattern for Form II is shown in FIG. 4 and the peaks are listed below in Table 2.

TABLE 2

X-ray powder diffraction pattern — Form II crystals

| Peak no. | Angle (deg.) | Tip width (deg.) | Peak intensity (cts.) | Back-ground (cts.) | D spacing (Ang) | I/Imax (%) | Sign |
|---|---|---|---|---|---|---|---|
| 1 | 3.025 | 0.07 | 424 | 48 | 29.1835 | 87.68 | 1.48 |
| 2 | 3.093 | 0.06 | 317 | 48 | 28.5467 | 65.46 | 1.48 |
| 3 | 5.8825 | 0.15 | 46 | 28 | 15.0121 | 12.57 | 3.31 |
| 4 | 8.4975 | 0.15 | 46 | 28 | 10.3973 | 9.55 | 0.83 |
| 5 | 10.293 | 0.24 | 45 | 40 | 8.5877 | 9.27 | 0.98 |
| 6 | 12.840 | 0.12 | 292 | 55 | 6.8890 | 60.42 | 0.78 |
| 7 | 14.943 | 0.15 | 350 | 135 | 5.9241 | 72.25 | 0.79 |
| 8 | 16.080 | 0.04 | 243 | 137 | 5.5075 | 50.28 | 0.87 |
| 9 | 16.465 | 0.24 | 339 | 142 | 5.3796 | 69.95 | 2.00 |
| 10 | 17.953 | 0.21 | 484 | 154 | 4.9370 | 100.00 | 2.69 |
| 11 | 18.193 | 0.12 | 342 | 159 | 4.8724 | 70.71 | 0.78 |
| 12 | 22.665 | 0.48 | 53 | 149 | 3.920 | 11.01 | 1.35 |
| 13 | 24.568 | 0.30 | 55 | 139 | 3.6206 | 11.31 | 1.02 |
| 14 | 29.573 | 0.96 | 38 | 106 | 3.0183 | 7.94 | 1.45 |

The present process provides a reproducible and rapid process straight through from the 4,7β-dimethyl-4-aza-5α-cholestan-3-one oil to Form I of 4,7β-dimethyl-4-aza-5α-cholestan-3-one. Thus, Form I may be directly produced by:

agitating 4,7β-dimethyl-4-aza-5α-cholestan-3-one oil, preferably containing residual solvent, preferably containing residual toluene, 5 to 10%, by weight, most preferably containing 5% by weight residual toluene, at a controlled temperature less than 60° C., preferably between 40° C. and 45° C.

Most preferably, the 4,7β-dimethyl-4-aza-5α-cholestan-3-one oil is seeded with polymorphic form I crystals of 4,7β-dimethyl-4-aza-5α-cholestan-3-one, 5 to 10% by weight; 10% by weight is especially preferred.

The present invention has the objective of providing methods of treating the hyperandrogenic conditions of androgenic alopecia including female and male pattern baldness, acne vulgaris, seborrhea, and female hirsutism by oral, systemic, parenteral or topical administration of a therapeutically effective amount of crystalline 4,7β-dimethyl-4-aza-5α-cholestan-3-one most preferably of polymorphic Form I. The term "treating androgenic alopecia" is intended to include the arresting and/or reversing of androgenic alopecia, and the promotion of hair growth.

The present invention has the further objective of providing methods of treating benign prostatic hyperplasia, prostatitis, and treating prostatic carcinoma by oral, systemic or parenteral administration of a therapeutically effective amount of crystalline 4,7β-dimethyl-4-aza-5α-cholestan-3-one most preferably of polymorphic Form I.

In the methods described above, the daily dosage of the compound of formula I may be varied over a wide range from 0.1 mg to 1,000 mg per adult human/per day. An effective amount of one of the novel compounds of this invention is ordinarily from about 0.002 mg/kg to 30 mg/kg of body weight per day, and more particularly the range is from about 0.01 mg/kg to 7 mg/kg of body weight per day.

The present invention also has the objective of providing suitable systemic, oral, parenteral and topical pharmaceutical formulations for use in the methods of treatment of the present invention. The compositions containing the active ingredient, crystalline 4,7β-dimethyl-4-aza-5α-cholestan-3-one preferably of polymorphic Form I, for use in the treatment of the above-noted hyperandrogenic conditions can be administered in a wide variety of therapeutic dosage forms in conventional vehicles for systemic administration. For example, the compounds can be administered in such oral dosage forms as tablets, capsules (each including timed release and sustained release formulations), pills, powders, granules, elixirs, tinctures, solutions, suspensions, syrups and emulsions. Likewise, they may also be administered in intravenous (both bolus and infusion), intraperitoneal, subcutaneous, topical with or without occlusion, or intramuscular form, all using forms well known to those of ordinary skill in the pharmaceutical arts. For oral administration, for example, the compositions can be provided in the form of scored or unscored tablets containing 0.1, 0.5, 1.0, 2.5, 5.0, 10.0, 15.0, 25.0, and 50.0 milligrams of the active ingredients for the symptomatic adjustment of the dosage to the patient to be treated.

For the treatment of androgenic alopecia including female and male pattern baldness, acne vulgaris, seborrhea, and female hirsutism, the crystalline compounds of the present invention also may be administered in a pharmaceutical composition comprising the active compound in combination with a pharmaceutically acceptable carder adapted for topical administration. Topical pharmaceutical compositions may be, e.g., in the form of a solution, cream, ointment, gel, lotion, shampoo or aerosol formulation adapted for application to the skin. Topical pharmaceutical compositions useful in the method of treatment of the present invention may include about 0.001% to 15% by weight of the active compound in admixture with a pharmaceutically acceptable carder such as alcohols, propylene glycol and mixtures thereof. Most preferably, the crystalline compounds of the present invention are formulated in topical pharmaceutical compositions at concentrations of 0.01% to 1.0% (w/w) in a pharmaceutically acceptable carder. A preferred pharmaceutically acceptable carder is composed of a mixture of propylene glycol, ethyl alcohol and water, most preferably about 30% propylene glycol, about 45% ethyl alcohol and about 25% water.

For the treatment of acne vulgaris, androgenic alopecia, seborrhea, female hirsutism, benign prostatic hyperplasia, prostatitis and the treatment of prostatic cancer, the crystalline compounds of the instant invention can be combined with a therapeutically effective amount of a 5α-reductase 2 inhibitor, such as finasteride, or a dual 5α-reductase 1 and 2 inhibitor, in a single oral, systemic, or parenteral pharmaceutical dosage formulation. Alternatively, a combined therapy can be employed wherein the crystalline compound of formula I and the 5α-reductase 2 inhibitor or the dual inhibitor are administered in separate oral, systemic, or parenteral dosage formulations. Also, for the skin and scalp related disorders of acne vulgaris, androgenic alopecia including male pattern baldness, seborrhea, and female hirsutism, the compound of the instant invention and a 5α-reductase 2 inhibitor or a dual inhibitor can be formulated for topical administration. For example, a crystalline compound of formula I and finasteride can be administered in a single oral or topical dosage formulation, or each active agent can be administered in a separate dosage formulation, e.g., in separate oral dosage formulations, or an oral dosage formulation of finasteride in combination with a topical dosage formulation of a crystalline compound of formula I. See, e.g., U.S. Pat. Nos. 4,377,584 and 4,760,071 which describe dosages and formulations for 5α-reductase inhibitors.

Furthermore, for the treatment of acne vulgaris and/or androgenic alopecia, a combined therapy can be used by administering a therapeutically effective amount of a compound of formula I in combination with a therapeutically effective amount of retinoic acid or a derivative thereof, e.g., an ester or amide derivative thereof, such as, e.g., tretinoin or isotretinoin.

Also, for the treatment of acne vulgaris, androgenic alopecia, seborrhea, female hirsutism, benign prostatic hyperplasia, prostatitis and the treatment of prostatic cancer, a combined therapy can be used by administering a therapeutically effective amount of a compound of formula I with a therapeutically effective amount of an anti-androgen, such as, e.g., flutamide, spironolactone or casodex.

For combination treatment with more than one active agent, where the active agents are in separate dosage formulations, the active agents can be administered concomitantly, or they each can be administered at separately staggered times.

Advantageously, the compounds of the present invention may be administered in a single daily dose, or the total daily dosage may be administered in divided doses of two, three or four times daily. The compounds for the present invention can be administered in intranasal form via topical use of suitable intranasal vehicles, or via transdermal routes, using those forms of transdermal skin patches well known to those of ordinary skill in that art. To be administered in the form of a transdermal delivery system, the dosage administration will, of course, be continuous rather than intermittent throughout the dosage regimen.

The dosage regimen utilizing the compounds of the present invention is selected in accordance with a variety of factors including type, species, age, weight, sex and medical condition of the patient; the severity of the condition to be treated; the route of administration; the renal and hepatic function of the patient; and the particular compound thereof employed. A physician or veterinarian of ordinary skill can readily determine and prescribe the effective amount of the drug required to prevent, counter, arrest or reverse the progress of the condition. Optimal precision in achieving concentration of drug within the range that yields efficacy without toxicity requires a regimen based on the kinetics of the drug's availability to target sites. This involves a consideration of the distribution, equilibrium, and elimination of a drug.

In the methods of the present invention, the crystalline compounds herein described in detail can form the active ingredient, and are typically administered in admixture with suitable pharmaceutical diluents, excipients or carriers (collectively referred to herein as "carrier" materials) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with an oral, non-toxic pharmaceutically acceptable inert carrier such as ethanol, glycerol, water and the like. Capsules containing the product of this invention can be prepared by mixing an active compound of the present invention with lactose and magnesium stearate, calcium stearate, starch, talc, or other carders, and placing the mixture in gelatin capsule. Tablets may be prepared by mixing the active ingredient with conventional tableting ingredients such as calcium phosphate, lactose, corn starch or magnesium stearate. Moreover, when desired or necessary, suitable binders, lubricants, disintegrating agents and, coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms. Include sodium oleate, sodium stearate, magnesium stearate, sodium benzoate, sodium acetate, sodium chloride and the like. Disintegrators include, without limitation, starch, methyl cellulose, agar, bentonite, xanthan gum and the like.

The liquid forms in suitably flavored suspending or dispersing agents such as the synthetic and natural gums, for example, tragacanth, acacia, methyl-cellulose and the like. Other dispersing agents which may be employed include glycerin and the like. For parenteral administration, sterile suspensions and solutions are desired. Isotonic preparations which generally contain suitable preservatives are employed when intravenous administration is desired.

Topical preparations containing the active drug component can be admixed with a variety of carrier materials well known in the art, such as, e.g., alcohols, aloe vera gel, allantoin, glycerine, vitamin A and E oils, mineral oil, PPG2 myristyl propionate, and the like, to form, e.g., alcoholic solutions, topical cleansers, cleansing creams, skin gels, skin lotions, and shampoos in cream or gel formulations. See, e.g., EP 0 285 382.

The compounds of the present invention can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

The compounds of the present invention may be coupled to a class of biodegradable polymers useful in achieving controlled release of a drug, for example, polylactic acid, polyepsilon caprolactone, polyhydroxy butyric acid, polyorthoesters, polyacetals, polydihydropyrans, polycyanoacrylates and cross-linked or amphipathic block copolymers of hydrogels.

In addition to the procedure described in WO 93/23419, 4,7β-dimethyl-4-aza-5α-cholestan-3-one oil may be prepared as described below:

Step 1:

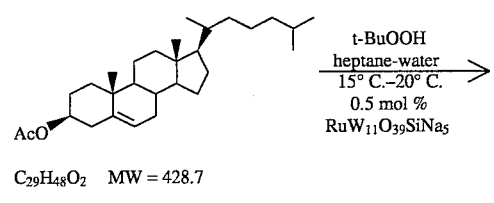

$C_{29}H_{48}O_2$  MW = 428.7

→ (t-BuOOH, heptane-water, 15° C.–20° C., 0.5 mol % RuW$_{11}$O$_{39}$SiNa$_5$) →

$C_{29}H_{46}O_3$  MW = 442.7

| Materials | Amt | Mole | MW |
| --- | --- | --- | --- |
| Cholesteryl acetate (95% Aldrich) | 78.1 gm | 0.173 | 428.7 |
| t-BuOOH (70 wt %, Aldrich) | 189 gm | 1.46 | 90.12 |
| Na$_2$WO$_4$ — 2H$_2$O | 3.3 gm | 0.010 | 329.9 |
| RuCl$_3$-xH$_2$O | 0.24 gm | 0.00116 | 207.43 |
| Sodium metasilicate (Na$_2$SiO$_3$) | 0.315 gm | 0.00258 | 122.06 |
| Sulfuric acid (d = 1.84 g/mL, 18M) | 0.45 mL | 0.0081 | 98.08 |
| Sodium sulfite (Na$_2$SO$_3$) | 39 gm | 0.309 | 126.04 |
| heptane | 300 mL | | |
| MEK (methyl ethyl ketone) | 550 mL | | |
| water | 460 mL | | |

In a 2000 mL 3-necked flask was added sodium tungstate dihydrate (3.3 gm), sodium metasilicate (0.315 gm) and 70 mL water and stirred until homogeneous. The solution was neutralized (pH =6–7) with concentrated sulfuric acid (0.45 mL). A 4° C. exotherm was noted for the addition of acid. Ruthenium trichloride hydrate (240 mg) was added and the mixture stirred for 10 min. Cholesteryl acetate (78.1 gm) and heptane (300 mL) were added to the catalyst mixture. The stirring rate was 225–275 rpm with an overhead paddle stirrer.

70% t-BuOOH (189 gm) was added over 5–10 min. An internal temperature of 15°–20° C. was maintained by cooling with a water bath. The temperature of the batch began to rise slowly after an induction period of 5–15 min. The reaction was stirred until less than 1.5 wt % of s.m. (starting material) and less than 2% of the 7-hydroxy cholesteryl acetate intermediate remained, about 20–24 hrs.

The reaction was monitored with a YMC basic column, 90:10 acetonitrile:water, flow rate=1.5 mL/min, UV detection at 200 nm. Retention times: $t_R$ cholesteryl acetate=17.0 min, $t_R$ 7-keto cholesteryl acetate=7.8 min, $t_R$ enedione 4.5 min, $t_R$ 7-hydroperoxides, 7-ols intermediates=6.8, 6.9, 7.0, 8.2 min. Later eluting impurities at 18 and 19 min are the 7-t-BuOO-cholesteryl acetates.

To the reaction mixture was added 550 mL MEK, 390 mL water, and 39 gms sodium sulfite. The mixture was heated to 70° C. until the enedione impurity was gone, about 3 hrs. The reaction mixture cooled, then was transferred to a separatory funnel and the aqueous layer cut and then the organic layer washed with 100 mL 1% brine. The MEK and t-BuOH were then removed by an azeotropic distillation with heptane (800 mL heptane added after an initial concentration to 300 mL) until less than 0.7% combined MEK and t-BuOH remained as assayed by GC (gas chromatography).

The heptane was checked for MEK and tBuOH levels by GC using an HP-5 column at 35° C. with a 0.5 mL flow rate. $t_R$ MEK=4.9 min, $t_R$ tBuOH=5.3 min, $t_R$ heptane=7.7 min. The volume was adjusted to 350 mL, cooled to −5° C. and filtered, washing twice with 150 mL 0° C. heptane. After drying, the product was obtained in 62% yield (51.5 gms total, 94 wt %, 97 A%) as an off-white solid. "A %" is area %.

Melting point (m.p.): 155°–157° C.

NMR ($^1$H, 300 MHz, CDCl$_3$): 5.70 (s, 1H), 4.7 (m, 1H), 2.5–0.8 (m, 43 H), 0.6 (s, 3H).

Step 2:

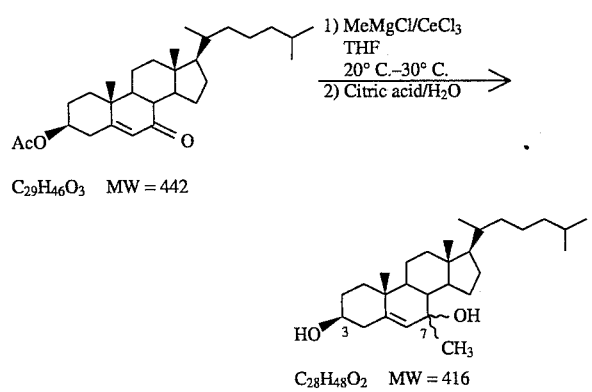

$C_{29}H_{46}O_3$  MW = 442

→ 1) MeMgCl/CeCl$_3$ THF 20° C.–30° C.  2) Citric acid/H$_2$O →

$C_{28}H_{48}O_2$  MW = 416

| Materials | Amt | Mole | MW |
| --- | --- | --- | --- |
| 7-keto-cholesteryl acetate (95% pure) | 60 g (as is) | 0.13 | 442 |
| Methyl magnesium chloride (3.0M) | 160 mL | 0.48 | |
| CeCl$_3$ (anhydrous) | 16.6 g | 0.068 | 245 |
| THF (KF = 50 µg/mL) | 300 mL | | |
| Citric acid | 115 g | 0.60 | 192 |
| water | 500 mL | | |
| toluene | 600 mL | | |
| sat'd NaHCO$_3$ | 240 mL | | |

Anhydrous cerium chloride (16.6 gm) was stirred as a slurry in THF (150 mL) at 20° C. under N$_2$ for 2 h.

The cerium chloride was obtained as the hepta-hydrate and dried in vacuo at an oven temperature of 170° C. for three to four days. The dried cerium chloride showed a weight loss of 0.7% by T.G. analysis. After two hours a sample of the slurry was removed and showed fine needles under a microscope. To the slurry was added the Grignard reagent (160 mL) and the resulting light purple mixture was aged for 30 minutes.

To the cooled mixture (20° C.) was added the ketone (60 gm at 95% purity, 57 gm by assay) in THF (150 mL) over 50 minutes while allowing the mixture to exotherm to 30° C. Addition of the ketone to the Grignard reagent was exothermic, the exotherm was controlled by the rate of addition. The ketone solution in THF should be warmed to 30° C. to ensure complete dissolution, prior to adding it to the Grignard reagent.

The reaction progress was monitored by HPLC (high pressure liquid chromatography). A 0.5 mL sample was added to 10 mL of 0.1N HOAc and then diluted to 50 mL with CH$_3$CN. HPLC conditions [Zorbax® phenyl column, CH$_3$CN, water, phosphoric acid; 75:25:0.1 gradient elution to 90:10:0.1 at 18 minutes, flow=1.5 mL/min, UV detection at 200 nm]. Retention times, 3,7-diol $t_R$=5.6 and 5.9 min, starting ketone $t_R$=10.9 min, intermediate 7-OH, 3-OAc $t_R$=9.8 and 10.8 min. There was about 95 area % of 3,7 diol (ca. 85 mg/mL). (NOTE: Any remaining starting material or reaction intermediates can be converted into product using additional Grignard reagent.)

Once complete, the reaction was quenched by adding it to a 0° C. mixture of citric acid solution (115 gm in 300 mL of water) and toluene (300 mL). The quench was exothermic. (NOTE: The rate of addition should be carefully controlled to maintain an internal temperature below 10° C.)

The two phase mixture was stirred for 30 minutes and allowed to stand for 10–15 minutes for an adequate phase separation. The pH of the aqueous layer was ca. 2. The organic phase was separated, washed with water (200 mL, pH=3 after washing) and saturated $NaHCO_3$ solution (240 mL, pH=8 after washing). This afforded 750 mL of an organic layer which contained 66 mg/mL of diol for a yield of 49.5 gm (93%). The aqueous layer contained less than 1% of product.

The batch was concentrated to 300 mL in vacuo (100–200 mm), diluted to 600 mL with toluene and re-concentrated to 360 mL. The solvent switch to toluene was considered complete when the G.C. area % of THF was <2% of the toluene area %. (NOTE: The first 200 mL of the distillation has a tendency to foam at low pressures. Once this phase is complete, the vacuum should be brought down to 100 mm. The distillation temperature slowly rises from 20° C. to ca. 45° C. as the solvent switch to toluene nears completion.)

Samples of the distillate were assayed for residual THF using G.C. A sample of ca. 0.1 mL was diluted to 1 mL with methanol. G.C. conditions: [HP-5 column (25M, 0.32 μm ID) using a heated block injector, 35° C. isothermal, flow= 0.5 mL/min], MeOH $t_R$=5.5 min, THF $t_R$=6.2 min, toluene $t_R$=10.1 min. The final assay was performed using a sample from the batch.

The organic layer contained 134.4 mg/mL of diols for a total yield of 48.4 gm (90%). (NOTE: The KF of the batch should be below 100 μg/mL before proceeding with the next step.)

Step 3: OPPENAUER OXIDATION

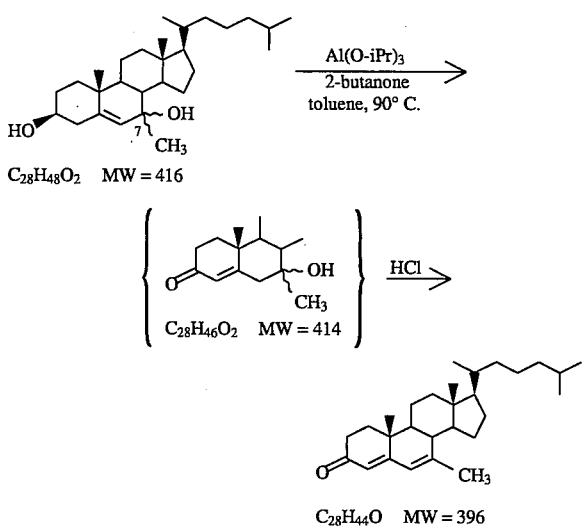

| Materials | Amt | MMole | MW |
|---|---|---|---|
| 7-methyl-7-hydroxy-cholesterol | 30.2 g | 72.6 | 416 |
| 2-butanone (d = 0.805, KF = 480 μg/mL) | 126 mL | 1404 | 72.11 |
| Aluminum isopropoxide | 18.9 g | 93 | 204.25 |
| 3N HCl | 120 mL | | |
| 5% NaCl solution | 120 mL | | |
| Conc. HCl | 3.5 mL | 42 | |

| | |
|---|---|
| D.I. water | 60 mL |
| Saturated $NaHCO_3$ | 60 mL |

To the toluene solution of the diol (256 mL, 118 mg/mL) was added 2-butanone (126 mL) and aluminum isopropoxide (18.9 g). The solution was heated to reflux (92° C.) under nitrogen. The reaction progress was monitored by HPLC.

The batch was assayed for 2-butanone content by G.C. prior to adding the aluminum isopropoxide. A sample of ca. 0.1 mL was diluted to 1 mL with MeOH. G.C. conditions [HP-5 column (25m, 0.32 μm ID) using a heated block injector at 250° C., column temp at 35° C. isothermal, flow=0.5 mL/min]2-butanone $t_R$=6.1 min, MeOH $t_R$=5.5 min, toluene $t_R$=10.1 min. The KF of the starting mixture was 70 μg/mL.

A 0.1 mL sample of the reaction mixture was quenched into 0.1N HOAc solution (2–3 mL) and then diluted to 10 mL with $CH_3CN$ in a volumetric flask. HPLC conditions [25 cm Zorbax® Phenyl column; $CH_3CN:H_2O$ with 0.1% phosphoric acid: 75:25 gradient elution to 90:10 at 18 min, hold 90:10 until 22 min; flow=1.5 mL/min, UV detection at 210 nm.] Starting diols $t_R$=5.4, 5.8 min, intermediate Δ-4 eneone $t_R$=6.4 min, dieneone $t_R$=12.1 min.

The reaction was considered complete when the level of starting diol was <3 area % (8 hours). Once complete the batch was cooled to 15°–20° C. and quenched with 3N HCl (120 mL). The two phase mixture was stirred for 20 min, and then allowed to settle. The lower aqueous layer was removed and the organic layer was washed with 5% NaCl (120 mL). The batch was concentrated in vacuo to one half volume (40°–60° C. at 150 mm). The distillation removed excess 2-butanone from the batch. The level of 2-butanone in the final batch was <2% of the toluene (using G.C.) and the KF was 60 μg/mL.

The toluene solution was treated with conc. HCl (3.5 mL) at 25° C., under N2. The reaction was assayed by HPLC until the intermediate tertiary alcohol was completely convened to dieneone (ca. 1 h). The solution was washed with D.I. water (60 mL) and saturated $NaHCO_3$ (60 mL). The pH of the bicarbonate wash was 8.5. (NOTE: The decomposition reaction will turn black if run for longer than 8 hours.) The resulting red solution (128 mL) contained 202 mg/mL of dienone for a yield of 25.9 gm (90%).

Step 4: TRANSFER HYDROGENATION

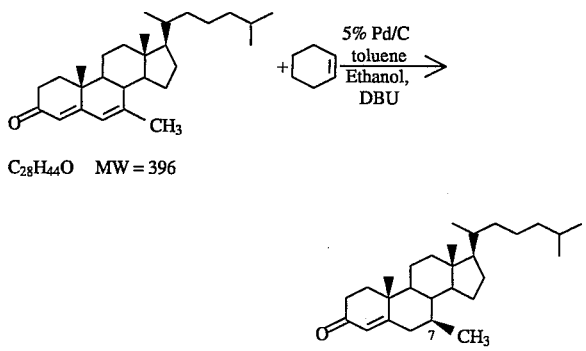

| Materials | Amt | MMole | MW |
|---|---|---|---|
| Dieneone (toluene solution) | 31.5 g | 79.5 | 396.7 |
| 5% Palladium on carbon (dry) | 4.5 g | | |
| Cyclohexene (d = 0.811) | 120 mL | 1.18 mole | 82.15 |

17
-continued

| 1,8 diazabicyclo[5.4.0] undec-7-ene (DBU) | 0.63 mL | 4.2 | 152.2 |
| Absolute ethanol | 495 mL | | |
| 3N HCl | 150 mL | | |
| half saturated NaHCO₃ | 100 mL | | |
| Solka Flok | | | |
| Hexanes | 250 mL | | |
| t-butanol | 175 mL | | |

The toluene solution of the dieneone (150 mL at 214.6 mg/mL) was diluted with ethanol (120 mL) and cyclohexene (120 mL) and DBU (0.62 mL). To the mixture was added 5% palladium on carbon (9.0 g of 50% water wet). The mixture was degassed using vacuum/nitrogen purges (3×). The slurry was then heated to reflux (reflux temperature=72° C.). The reaction was monitored by HPLC.

A 2 mL sample of the reaction mixture was filtered through Solka Floc. The filtrate (0.1 mL) was diluted to 10 mL with $CH_3CN$ and analyzed by HPLC: 25 cm Zorbax® phenyl column; acetonitrile/water containing 0.1% phosphoric acid: gradient elution from 75:25 to 90:10 $CH_3CN$:water in 18 min, hold 90:10 until 22 min; flow=1.5 mL/min; UV detection at 200 nm.

Dienone $t_R$=12.1 min, Δ-4 enone $t_R$=13.2 min, Δ-5 enone $t_R$=14.1 min, over-reduced ketone $t_R$=14.4 min, ethyl enol ether $t_R$=20.9 min. The over-reduced ketone should be assayed at 192 nm.

The reaction was considered complete when the dieneone level was <2 A % and the Δ-5 enone level was 5% (about 10 hours). When the reaction was complete the mixture was cooled to ambient temperature. The palladium was removed by filtration through Solka Floc and the filter cake was washed with ethanol (150 mL).

The batch contained 51 mg/mL of enone. (NOTE: Prolonged reaction times should be avoided since over-reduction can occur. If the starting material has been consumed and the level of Δ-5 enone is >5% after 10 hours, then the palladium should be filtered, and the isomerization completed without catalyst present.)

The solution was concentrated under reduced pressure (75 mm) to a volume of approximately 150 mL. The batch was diluted with ethanol (225 mL) and re-concentrated to 150 mL.

The solvent switch to ethanol was considered complete when the toluene level was <2% of the ethanol by G.C., and there was no detectable cyclohexene. (NOTE: Removal of cyclohexene is important since it reacts in the subsequent oxidative cleavage step and unproductively consumes periodate.) A 0.1 mL sample was diluted to 1 mL with ethanol for the cyclohexene assay (and 1,1,1 trichloroethane for the toluene assay). G.C. conditions [HP-5 (25M×0.32 μm ID), using a heated block injector at 250° C., column temp at 35° C. isothermal, flow=0.5 mL/min] ethanol $t_R$=5.6 min, cyclohexene $t_R$=7.7 min, trichloroethane $t_R$=7.7 min, toluene $t_R$=10.2 min. The presence of cyclohexene is also detectable by ¹H NMR (CDCl₃) of the solution: cyclohexene vinyl protons at δ=5.64 ppm, eneone vinyl proton at δ=5.69 ppm.

The concentrate was diluted with hexanes (250 mL) and 3N HCl (150 mL). The two phase mixture was warmed to 40° C. until enol ether hydrolysis was complete. The layers were separated and the organic layer was washed with half saturated sodium bicarbonate (100 mL). The hexane phase had a volume of 291 mL, contained less than 5% ethanol by volume and assayed for 92 mg/mL of enone.

The solution was concentrated to 100 mL under reduced pressure (100 mm/15° C.). The batch was diluted with t-butanol (175 mL) and re-concentrated to 100 mL (100

18 mm/40° C.). The batch contained 260 mg/mL of the desired 7-β-methyl enone for a yield of 26.8 gm (85%).

(NOTE: These compounds could also be detected by G.C.M.S. Use of G.C. to follow this reaction should be avoided since the enone disproportionates on the column. G.C.M.S. conditions [HP-5 (25M) column, on column injection at 285° C. isothermal]; over-reduced enone $t_R$=12.8 min, 7 alpha-epimer $t_R$=15.7 min, product $t_R$=17.3 min, s.m. $t_R$=21.3 min.

Step 5: OXIDATIVE CLEAVAGE

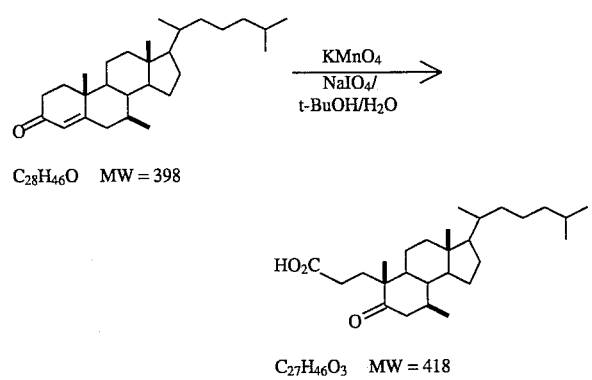

| Materials | Amt | Mol | MW |
|---|---|---|---|
| 7-β-Methylcholest-4-ene-3-one | 300 gm | 0.75 | 398 |
| t-Butanol (d = 0.786) | 6.6 L | | |
| Sodium carbonate | 159 g | 1.5 | 106 |
| Sodium periodate | 1550 g | 7.2 | 213.9 |
| Potassium permanganate | 11.1 g | 0.07 | 158 |
| D.I. Water | 14.2 L | | |
| Diatomite | 50 g | | |
| Ethyl acetate (d = 0.902) | 2.6 L | | |
| Heptane (d = 0.684) | 5.0 L | | |
| conc. Hydrochloric acid | 250 mL | | |
| 5% Aqueous NaCl | 2.5 L | | |
| Acetic acid (d = 1.049) | 9.0 L | | |

In a 5 L roundbottom flask was charged D.I. water (4.93 L), sodium periodate (1.55 kg) and potassium permanganate (11.1 g). The slurry was stirred at 65° C. for 30 minutes to obtain complete solution.

To a solution of the enone (300 g) in t-butanol (4.60 L) was added a solution of sodium carbonate (159 g) in water (2.3 L). The two phase mixture was warmed to 65° C. The enone should be toluene, ethanol and cyclohexene free. (NOTE: Concentration of enone in organic layer is about 56 mgmL.⁻¹.) The sodium periodate solution was added to the enone solution over 3 h with rapid stirring, maintaining the reaction temperature at 65° C. The slurry was aged at 65° C. for 2 h. The periodate solution was added via a heated addition funnel.

Carbon dioxide gas was evolved during the reaction. A slow addition ensures controlled gas evolution. No exotherm was detected during addition. During the addition a purple/brown slurry was formed.

The reaction progress was monitored by HPLC. A 2 mL sample of the reaction mixture was cooled to 15° C. and filtered. The filtrate (0.1 mL) was diluted to 10 mL with water/$CH_3CN$ (1:3). HPLC conditions [YMC Basic 25 cm×4.6 mm, $CH_3CN$, 0.01M $H_3PO_4$; 90:10 isocratic flow= 1.5 mL/min, UV detection at 200 nm]; enone $t_R$=11.5 min, seco-acid $t_R$=5.5 min.

The reaction was considered complete when the starting enone was <0.5mg/mL. Water (3.0 L) was added and the slurry heated to reflux for 2 h to decompose any remaining KMnO₄ (color change from purple to brown) and to dissolve most of the solids precipitated on the vessel walls. The resultant slurry was cooled to 15° C. and filtered through dicalite (50 g). The vessel and cake were washed with t-butanol/water (1:2, 6.0 L).

The filter cake was assayed for seco acid by dissolving 200–400 mg of cake with 50 mL water and 50 mL acetonitrile then filtering into the sample vial through diatomite to remove the small amount of orange manganese solids. The filtrates (pH=9.0–10.5) were extracted with heptane (5.0 L).

Ethyl acetate (2.6 L) was added to the aqueous mixture and the pH adjusted to 2.5±0.3 by the addition of conc. HCl (250 mL). The aqueous layer was removed.

The organic layer was washed with 5% aqueous brine (2×1.2 L). The ethyl acetate solution was concentrated (150 mm. Hg, 30° C.) to approx 10% volume. Acetic acid (7.4 L) was added and the residual ethyl acetate removed by concentration (100 mm. Hg, 60° C.) to <1% by volume (<0.5 area % by HPLC). The final volume was adjusted to 5.0 L by addition of acetic acid. Ethyl acetate removal was monitored by HPLC using the conditions above except the flow rate was 0.5 mL/min and UV detection at 210 nm. Ethyl acetate $t_R$=7.4 min, acetic acid . $t_R$=6.9 min. The assay yield was 275 gm which represented an 88% yield. The acetic acid solution was used directly in the following step (ene-lactam formation).

Step 6: NH-Enelactam Formation

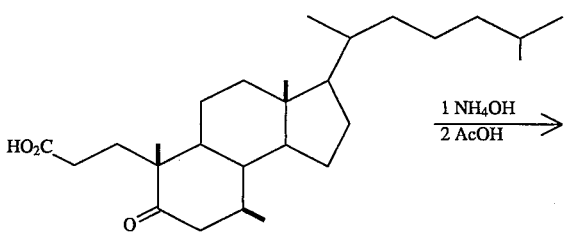

$C_{27}H_{46}O_3$  MW = 418

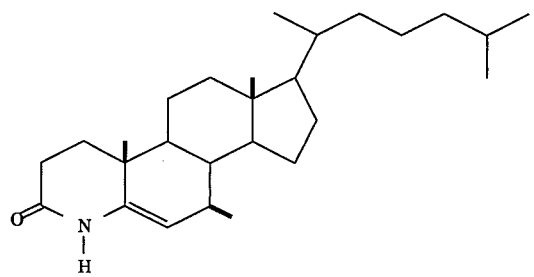

$C_{28}H_{47}NO$  MW = 399

| Materials | Amt | Mole | MW |
| --- | --- | --- | --- |
| Seco-acid | 265 g | 0.634 | 418 |
| Ammonium Acetate | 488 g | 6.33 | 77.1 |
| 2,6-di-t-butyl-4-methylphenol (BHT) | 5.3 g | 0.024 | 220 |
| D.I. Water | 565 mL | | |
| Acetic acid | 833 mL | | |

To a solution of seco-acid in acetic acid (265 g in 5.3 L) obtained in the previous step was added BHT (5.3 g) and ammonium acetate (488 g) at 20° C. The slurry was warmed to a gentle reflux under a nitrogen atmosphere for 3 h. Complete solution was obtained at 30° C. The internal temperature was 120° C. at reflux. Color changed from yellow to dark red/brown. Use of reduced amounts of acetic acid results in oiling of the product at the crystallization stage.

The reaction progress was monitored by HPLC. HPLC conditions [SB Phenyl, CH₃CN, 0.01M H₃PO₄; isocratic 80:20 for 30 min, flow=1.5 mL/min, UV detection at 190/200 nm] Retention times: ene-lactam $t_R$=9.4 min, seco acid $t_R$=5.3 min. UV detection was at 190 nm for reaction progress and 200 nm for s.m. and product assay. The reaction was considered complete when <0.05 A % seco acid remained, about 3–4 hrs.

The reaction mixture was cooled to 60° C. and water (398 mL) added over 15 min. (NOTE: Addition of exactly 7.5% v/v water to the acetic acid solution is important.) The solution was allowed to cool to 50° C. and seeded with ene-lactam (1.0 gm). Crystallization occurred at 50° C. The slurry obtained was aged at 50° C. for 1 h and then cooled to 0°–2° C. over 2 h.

The slurry was filtered and the light tan solid washed with 5:1 acetic acid/water (1.0 L). The solid was dried in vacuo at 30° C. overnight to give 255 gm at 87 wt % by assay (remainder is acetic acid) for an 88% yield. HPLC profile, UV at 200 nm was 99.4 A %. Melting point (m.p.) of solvate=112°–115° C. Pure m.p.=175°–178° C., softens at 162° C.

Step 7: NH-Enelactam Recrystallization

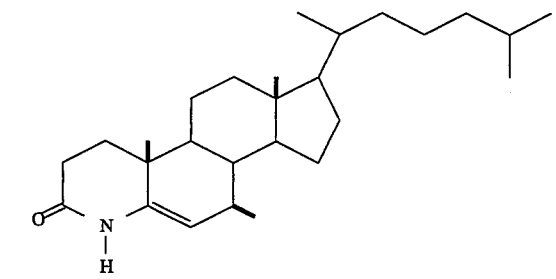

$C_{28}H_{47}NO$  MW = 399

| Materials | Amt | Mole | MW |
| --- | --- | --- | --- |
| Enelactam | 20 g | 0.041 | 400 |
| D.I. Water | 17 mL | | |
| Acetic acid | 133 mL | | |
| BHT | 0.20 g | 0.00091 | 220 |

To 20 gm at 83 wt % enelactam was added 100 mL acetic acid which contained 200 mg of BHT. The slurry was warmed to 60° C. under a nitrogen atmosphere to achieve dissolution, then cooled to 50° C. A charge of 10 mL water was then added. The mixture was then cooled to 5° C. over 1.5 hrs, aged for one hour and then the solid filtered off. (NOTE: The solution at 50° C. should have started crystallizing before cooling to 5° C.) The solution Kf after BHT addition was about 0.2–0.4% w/w.

The mother liquor amounts were monitored by HPLC. HPLC conditions [SB Phenyl, CH₃CN, 0.01M H₃PO₄; isocratic 80:20 for 30 min, flow=1.5 mL/min, UV detection at 200 nm] Retention times: ene-lactam $t_R$=9.4 min. Sample 100 μL and dilute to 10 mL with acetonitrile.

The slurry was filtered and the light tan solid washed with 5:1 acetic acid/water (40 mL) at 5° C. The solid was dried in vacuo at 30° C. overnight to give 18.5 g at 84 wt % by assay (remainder is acetic acid) for a 94% recovery. HPLC profile, UV at 200 nm was 99.4.A %

M.p. solvate is 112°–115° C. Pure m.p. is 175°–178° C., softens at 162° C.

Step 8: N—H Enelactam Reduction

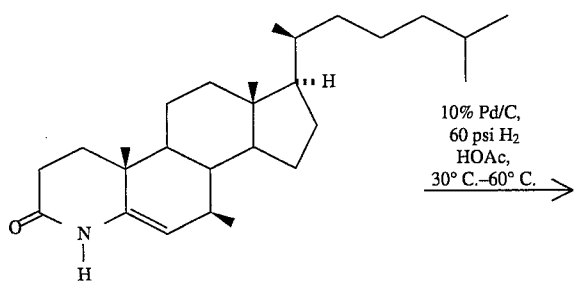

$C_{27}H_{45}NO$  MW = 399.6

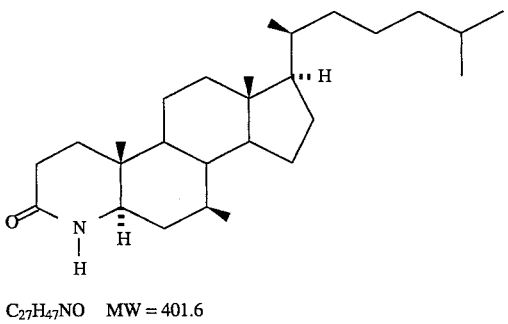

$C_{27}H_{47}NO$  MW = 401.6

| Materials | Amount | Mol | MW |
|---|---|---|---|
| Enelactam (87 wt %) | 190.0 g | 0.475 | 399.64 |
| HOAc (d = 1.05) | 3.8 L | | |
| BHT | 3.8 g | 0.017 | 220.4 |
| 10% Pd/C (50% wet) | 38 g | 10 wt % | |
| Hydrogen | 60 psi | | |
| Heptane | 3.8 L | | |
| MEK | 2.65 L | | |

BHT (3.8 gm) was dissolved in acetic acid (1.71 L) at 20° C. The solution was degassed with nitrogen purge for 30 min and the enelactam (218 g at 87 wt %) added in one portion. The resultant solution was purged with nitrogen for 15 minutes. 10% Pd/C (50% wet) (38 g) was added and the slurry transferred to a 1 gallon stirred autoclave. Degassed acetic acid (190 mL) was used to rinse the slurry into the autoclave. (NOTE: BHT must be added to the acetic acid prior to addition of the ene-lactam. The use of BHT stabilized acetic acid is necessary due to the oxidative instability of the ene-lactam.)

After vacuum purging with nitrogen the mixture was placed under 60 psi $H_2$ and stirred at 20° C. After 10 h at 20° C. the reaction temperature was increased to 60° C. until reaction was >99.9% complete.

The reaction was monitored by HPLC, [25.0 cm Zorbax® phenyl SB, 90:10 $CH_3CN$: 0.01% $H_3PO_4$, 1.5 mL/min, Dual UV detection at 210 nm and 240 nm]. Retention times: enelactam 8.50 min, trans-lactam 12.4 min, cis-lactam 18.4 min. Sample 20 μL and dilute to 2 mL with acetonitrile.

On complete reaction (ie, >99.9% conversion) the mixture was cooled to 20° C. and filtered through Solka-Flok (20 gm). The cake was washed with acetic acid (1.9 L). The filtrates were combined and concentrated at 30° C./10 mm.Hg to a volume of 570 mL. Heptane (total of 3.8 L) was added and concentration continued at atmospheric pressure (azeotrope b.p.=91°–92° C.) to remove the acetic acid. (NOTE: Removal of the acetic acid to <0.2% by volume is important due to the very high solubility of the product in acetic acid.) Final b.p. was 98–99° C. Acetic acid was monitored at 200 nm by HPLC using a 25.0 cm Zorbax® phenyl SB column with 90:10 $CH_3CN$:water, 0.5 mL min$^{-1}$ as eluent. Sample 100 μL and dilute to 10 mL with acetonitrile.

The solution was concentrated to 570 mL and MEK (total of 2.5 L) added. The heptane was removed by azeotropic distillation at atmospheric pressure to <5% by volume as determined by G.C. of distillates and batch. G.C. Conditions: DB-5 20m. 0.5 mL min$^{-1}$ Helium, 35° C. isothermal; MEK $t_R$=6.4, heptane $t_R$=8.0 min. Crystallization occurs during removal of heptane.

(Alternatively, the compound may be crystallized directly from acetic acid without switching the solvent from acetic acid to heptane to MEK.)

The volume was adjusted to 600 mL and the solution was allowed to cool to 20° C. over 3 h. The resultant slurry was aged at −10° C. for 2 h. The solid was collected on a filter frit and washed with cold MEK (150 mL). The solid was dried in vacuo at 20° C. Yield 170 g, at >99 wt %; >99.2 A % at 210 nm. Step yield 89%.

Step 9: Methylation

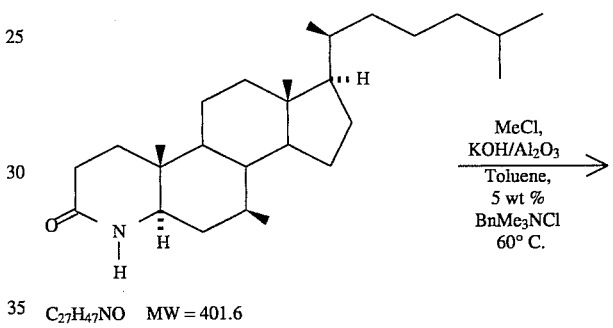

$C_{27}H_{47}NO$  MW = 401.6

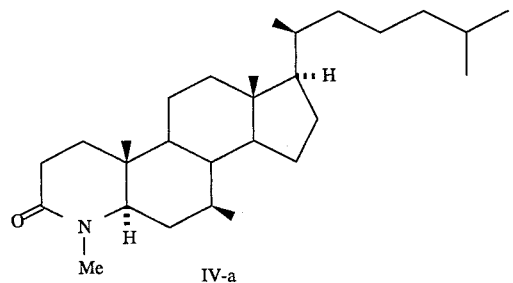

IV-a $C_{28}H_{49}NO$  MW = 415.7

| Materials | Amount | Mol | MW |
|---|---|---|---|
| N—H Lactam | 3.0 kg | 7.47 | 401.6 |
| Methyl chloride | 453 g | 8.96 | 50.5 |
| KOH/Alumina[1:1] | 3.0 kg | 22.8 | 56 |
| BnMe3NCl | 150 g | 0.81 | 185.7 |
| Toluene (d = 0.867) | 14.0 L | | |

A 5 gallon autoclave was charged with a slurry of lactam (3.0 kg), BnMe3NCl (150 g) and potassium hydroxide on alumina (1:1, 3.0 kg) in toluene (12 L) at room temperature. Methyl chloride (453 g) was introduced at 20° C. with slow stirring. The slurry was heated to 65° C. with slow stirring and aged for 1 h. An exotherm at 52° C. of about 3° C. was noted as a spike on the temperature recorder.

The reaction progress was monitored by HPLC. HPLC conditions [Zorbax® SB phenyl, $CH_3CN$, 0.01M $H_3PO_4$; 90:10 isocratic, flow=1.5 mL/min, UV detection at 200 nm] lactam $t_R$=12.4 min, IV-a $t_R$=15.0 min. 25 μL Sample of toluene layer was diluted to 2 mL with acetonitrile. The reaction was monitored until complete conversion was obtained (>99.95%). The reaction was complete in <60 min at 60° C.

The reaction mixture was cooled to 20° C. and purged with nitrogen (4×) to remove any excess MeCl. The toluene solution was filtered through Solka Floc (100 gm) and the vessel and cake washed with toluene (2 L). The combined filtrates were concentrated at 100 mm. Hg and 20°–30° C. to a residual oil. The oil should be homogeneous in heptane (10 mLg$^{-1}$) without any cloudiness.

The oil was assayed for toluene by G.C. oven temp 35° C. isothermal. The product (100 mg) was dissolved in methanol (0.5 mL) and 1 μL injected. Toluene $t_R$=4.4 min, methanol $t_R$=2.7min.

Representative experimental procedures further illustrating the process of the present invention are detailed below. These are exemplary procedures and should not be construed as being limitations on the novel process of the present invention.

GENERAL EXPERIMENTAL PROCEDURE FOR CRYSTALLIZATIONS USING LIST DISCOTHERM MIXER

1. The List Discotherm mixer was filled with about 1 kg of 4,7β-dimethyl-4-aza-5α-cholestan-3-one oil or amorphous solid, corresponding to a fill volume of about 50%.

2. If amorphous solid 4,7β-dimethyl-4-aza-5α-cholestan-3-one was employed in Step 1, above, the contents of the List Discotherm mixer were melted in situ by applying an 85° C. water-glycol bath on the jacket. Regardless of the starting form of the 4,7β-dimethyl-4-aza-5α-cholestan-3-one material, a nitrogen atmosphere was maintained at all times. The weight of the material in the mixer was based on the original charge plus any additional charges prior to melting.

3. If the Example involves toluene, the amount of toluene present was determined by thermogravimetric analysis (TG) and/or HPLC. The toluene level was adjusted by adding additional toluene. Samples were taken to confirm the desired level.

4. The amount of seed required was based on the weight of the oil and the desired seed content. Seed crystals were of Form I. Seed was typically added below 25° C. The oil and seed were mixed for 5–10 minutes at 67 RPM before the t=0 sample was taken, unless noted otherwise.

5. The RPM of the mixer and the jacket temperature were set and the experiment was started. The batch temperature was recorded every half hour. If the batch temperature increased above 45° C., the RPM of the mixer was reduced since the rate of heat transfer between the jacket and the batch is limited.

6. The mixer was sampled periodically to profile the crystallization. The frequency of sampling was based on the expected rate of crystallization. Samples were nm on DSC (differential scanning calorimetry).

EXAMPLE 1

Preparation of 4,7β-dimethyl-4-aza-5α-cholestan-3-one Form I 4,7β-dimethyl-4-aza-5α-cholestan-3-one oil (1 kg) is heated and added to the List Discotherm Mixer under an inert atmosphere. The level of residual toluene is measured and additional toluene is added to bring the level to 5 weight % toluene. The jacket temperature of the mixer is set at 5° C. 4,7β-dimethyl-4-aza-5α-cholestan-3-one Form I seed (100 g, 10% by weight) is added to the mixture at 67 rpm. The seeded mixture is agitated for 1 hour at 67 rpm and is aged with no agitation for 30 minutes. A sample is taken to confirm greater than 90% crystallization (Form I). The batch temperature is constant throughout agitation at 43° C. to 47° C. One kilogram of 0° to 5° C. cold water is added and the slurry is removed from the mixer into a WARING blender for size reduction. The WARING blender (manufactured by the Waring Products Division of Dynamics Corporation of America)is run for 2 to 3 minutes at high speed. The slurry is filtered through a filter funnel. The crystalline product is washed with water and dried under vacuum.

EXAMPLES 2–7

Preparation of 4,7β-dimethyl-4-aza-5α-cholestan-3-one Form I -varying seed level The following were conducted with solvent-free (<0.6%) oil of 4,7β-dimethyl-4-aza-5a-cholestan-3-one. All experiments were begun with a mixing rate of 67 RPM. The mixer stayed at 67 RPM for Examples 2, 3, 6. The rate of mixing was reduced to 37 RPM in Example 4. The rate of mixing was reduced to 35 RPM and then 17 RPM in Example 5, and the rate of mixing was reduced to 33 RPM in Example 7. Mixing was reduced due to increasing temperatures; RPM was decreased in order to maintain the temperature under 45° C. Heat was attributed to the increased viscosity of the melt. Heat transfer of the List laboratory unit was limited by the surface area of the jacket and the coating of viscous material on the jacket surface. All experiments were carded out over a temperature range of 24° to 52° C.

| Example | Seed Level Weight % | Induction Time (hours) | Rate of Crystallization %/hour |
| --- | --- | --- | --- |
| 2 | 0 | ≈5 | 0.7 |
| 3 | 1 | ≈4 | 4 |
| 4 | 5 | ≈2 | 7 |
| 5 | 10 | ≈1 | 26 |
| 6 | 15 | ≈1 | 25 |
| 7 | 20 | ≈1.5 | 18 |

In each Example above, a sample of the 4,7β-dimethyl-4-aza-5α-cholestan-3-one oil was taken before adding the seed. Each crystallization profile can be broken down into two separate regions: the first where the rate of crystallization was about zero, and the second where the rate of crystallization was maximum. The time span for the first region is defined as the induction time. As seed level increases from 0% to 10%, induction time decreased and rate of crystallization increased. Above 10%, both the induction time and rate of crystallization did not change significantly with seed level.

The lower crystallization rate and the longer induction time at 20% seed level, compared to 10% and 15% seed levels, are not readily explained but may be due to scatter in the 20% data. It is important to note that in all of the above experiments, the last data point is at or near the point where agitation by the List Discotherm mixer either stopped or was significantly reduced. This is due to the significant increase in the viscosity of the batch with increased crystallinity. At this point the experiment was either terminated, or aged without mixing to verify completion of crystallization. The percent crystallinity did not change with static aging of >24 hours for the 10% seed experiment demonstrating that conversion was complete during the 4 hours of mixing. Static aging for the 1% and 5% studies resulted in percent crystallinity of >90%.

EXAMPLES 8 AND 9

Preparation of
4,7β-dimethyl-4-aza-5α-cholestan-3-one Form I

Experiments were conducted with 5% toluene and 10% by weight seed loading. In both of these experiments, the induction time disappeared and maximum crystallization rates increased significantly compared to previous experiments without toluene.

Example 8–5% toluene

The mixer was run at 67 RPM and temperature was maintained between 14° to 35° C. Eighty percent crystallinity was achieved in about an hour and 90% crystallinity in less than 3.5 hours. The product removed from the mixer was a soft, crumbly, and easily-handled solid.

Example 9–10% toluene

The mixer was run at 67 RPM and the temperature was maintained between 15° to 26° C. The initial crystallization rate was very high, but the crystallinity of the batch leveled off around 50%. This may be because the toluene may be dissolving some of the newly-formed crystals. The product removed from the mixer was a soft, crumbly, and easily-handled solid.

EXAMPLES 10 AND 11

| | | | | | | |
|---|---|---|---|---|---|---|
| | | Effect of Agitation level on crystallization of 4,7β-dimethyl-4-aza-5a-cholestan-3-one Form I | | | | |
| Example | RPM of Mixer | Toluene Level Weight % | Toluene Level Weight % | Temperature °C. | Induction Time (hours) | Rate of Crystallization %/hour |
| 10 | 57 | 10 | 0.9 | 36–43 | ≈0.5 | 16 |
| 11 | 10 | 8 | 0 | 34–42 | ≈3.5 | 1.4 |

EXAMPLE 12

Preparation of
4,7β-dimethyl-4-aza-5α-cholestan-3-one-mixture
Form I and Form H

A solution of 4,7β-dimethyl-4-aza-5α-cholestan-3-one (98.0 g) in toluene is concentrated under vacuum to less than 5 weight percent toluene. Seed crystals of 4,7β-dimethyl-4-aza-5α-cholestan-3-one Form I (20 mg) are added to the concentrate. The mixture is aged under vacuum for 3 to 7 days. The resultant solid is a mixture of crystalline Form I and Form It.

EXAMPLE 13

Formulation example

Preparation of a topical formulation of 4,7β-dimethyl-4-aza-5α-cholestan-3-one Form I 0.01% active ingredient

| Components: | Per mL |
|---|---|
| 4,7β-dimethyl-4-aza-5α-cholestan-3-one Form I | 0.0936 mg |
| Propylene Glycol USP | 317.74 mg |
| Ethyl Alcohol 200 Proof USP | 363.13 mg |
| Purified Water USP | 255.08 mg |
| Composition of inactive formulation: | |
| Propylene Glycol USP | 317.43 mg |
| Ethyl Alcohol 200 Proof USP | 362.73 mg |
| Purified Water USP | 254.83 mg |

4,7β-dimethyl-4-aza-5α-cholestan-3-one Form I is combined with about 50% of the final volume of inactive formulation in a suitable glass container and mixed thoroughly. After complete dissolution of 4,7β-dimethyl-4-aza-5α-cholestan-3-one Form I, the final total weight is adjusted by adding inactive formulation. The solution is filled into USP Type I clear glass vials and fitted with teflon coated rubber stoppers and sealed with aluminum caps.

EXAMPLE 14

Formulation example

Preparation of a topical formulation of 4,7β-dimethyl-4-aza-5α-cholestan-3-one Form I 0.1% active ingredient

| Components: | Per mL |
|---|---|
| 4,7β-dimethyl-4-aza-5α-cholestan-3-one Form I | 0.936 mg |
| Propylene Glycol USP | 317.45 mg |
| Ethyl Alcohol 200 Proof USP | 362.75 mg |
| Purified Water USP | 254.85 mg |

Composition of inactive formulation:

| Components: | Per mL |
|---|---|
| Propylene Glycol USP | 317.43 mg |
| Ethyl Alcohol 200 Proof USP | 362.73 mg |
| Purified Water USP | 254.83 mg |

4,7β-dimethyl-4-aza-5α-cholestan-3-one Form I is combined with about 50% of the final volume of inactive formulation in a suitable glass container and mixed thoroughly. After complete dissolution of 4,7β-dimethyl-4-aza-5α-cholestan-3-one Form I, the final total weight is adjusted by adding inactive formulation. The solution is filled into USP Type I clear glass vials and fitted with teflon coated rubber stoppers and sealed with aluminum caps.

EXAMPLE 15

Preparation Of a tablet of
4,7β-dimethyl-4-aza-5α-cholestan-3-one Form I

As a specific embodiment of an oral composition of a compound of this invention, 5 mg of 4,7β-dimethyl-4-aza-5α-cholestan-3-one Form I is formulated with sufficient finely divided lactose to provide a total amount of 580 to 590 mg to fill a size 0 hard gelatin capsule.

Biological Assays

Preparation of Human prostatic and scalp 5α-reductases.

Samples of human tissue were pulverized using a freezer mill and homogenized in 40 mM potassium phosphate, pH 6.5, 5 mM magnesium sulfate, 25 mM potassium chloride, 1 mM phenylmethylsulfonyl fluoride, 1 mM dithiothreitol (DTT) containing 0.25M sucrose using a Potter-Elvehjem homogenizer. A crude nuclear pellet was prepared by centrifugation of the homogenate at 1,500×g for 15 min. The crude nuclear pellet was washed two times and resuspended in two volumes of buffer. Glycerol was added to the resuspended pellet to a final concentration of 20%. The enzyme suspension was frozen in aliquots at −80° C. The prostatic and scalp reductases were stable for at least 4 months when stored under these conditions.

5α-reductase assay.

The reaction mixture for the type 1 5α-reductase contained 40 mM potassium phosphate, pH 6.5, 5 gM [7-$^3$H]-testosterone, 1 mM dithiothreitol and 500 μM NADPH in a final volume of 100 μl. The reaction mixture for the type 2 5α-reductase contained 40 mM sodium citrate, pH 5.5, 0.3 μM [7-$^3$H]-testosterone, 1 mM dithiothreitol and 500 μM NADPH in a final volume of 100 μl. Typically, the assay was initiated by the addition of 50–100 μg prostatic homogenate or 75–200 μg scalp homogenate and incubated at 37° C. After 10–50 min the reaction was quenched by extraction with 250 μl of a mixture of 70% cyclohexane: 30% ethyl acetate containing 10 μg each DHT and T. The aqueous and organic layers were separated by centrifugation at 14,000 rpm in an Eppendorf microfuge. The organic layer was subjected to normal phase HPLC (10 cm Whatman partisil 5 silica column equilibrated in 1 ml/min 70% cyclohexane: 30% ethyl acetate; retention times: DHT, 6.8–7.2 min; androstanediol, 7.6–8.0 min; T, 9.1–9.7 min). The HPLC system consisted of a Waters Model 680 Gradient System equipped with a Hitachi Model 655A autosampler, Applied Biosystems Model 757 variable UV detector, and a Radiomatic Model A120 radioactivity analyzer. The conversion of T to DHT was monitored using the radioactivity flow detector by mixing the HPLC effluent with one volume of Flo Scint 1 (Radiomatic). Under the conditions described, the production of DHT was linear for at least 25 min. The only steroids observed with the human prostate and scalp preparations were T, DHT and androstanediol.

Inhibition studies

Compounds were dissolved in 100% ethanol. IC$_{50}$ values represent the concentration of inhibitor required to decrease enzyme activity to 50% of the control. IC$_{50}$ values were determined using a 6 point titration where the concentration of the inhibitor was varied from 0.1 to 1000 nM.

Representative compounds of this invention were tested in the above described assay for 5α-reductase type 1 and type 2 inhibition. For the inhibition of 5α-reductase type 1, the compounds have IC$_{50}$ values lower than 600 nM, with the majority of compounds having IC$_{50}$ values ranging from about 0.3 nM to about 200 nM. For the inhibition of 5α-reductase type 2, the same compounds have IC$_{50}$ values greater than about 155 nM, with the majority of compounds having IC$_{50}$ values greater than 1000 nM. Each compound has at least a 2-fold greater selectivity for inhibition of 5α-reductase type 1 over type 2, with the majority of the compounds having a 10-fold or greater selectivity for inhibition of 5α-reductase type 1 over type 2. These results demonstrate the utility of the compounds of the instant invention for the treatment of hyperandrogenic conditions.

A compound referred to herein as a 5α-reductase 2 inhibitor is a compound that shows inhibition of the 5α-reductase 2 isozyme in the above-described assay.

Human Dermal Papilla Cell Assay

The dermal papilla is a small group of cells at the base of each hair follicle, and it is presently thought that these cells are stem cells that form the basis for hair growth. These cells have been shown to have 5 alpha reductase activity, and it is therefore possible to test inhibitors of 5 alpha reductase in these cell culture systems.

Isolated and cultured dermal papilla cells are prepared according to the methods of Messenger, A.G., *The Culture of Dermal Papilla Cells Front Human Hair Follicles*, Br. J. Dermatol. 110:685–689, 1984 and Itami, S. et. al., *5α-Reductase Activity In Cultured Human Dermal Papilla Cells From Beard Compared With Reticular Dermal Fibroblasts*, J. Invest. Dermatol. 94:150–152, 1990. Beard dermal papilla cells and occipital scalp hair of two different individuals are used throughout the study. All experiments are performed at confluency after the fourth to sixth subculture. Confluent monolayers are rinsed twice with phosphate-buffered saline, scraped from dishes by rubber policemen, and collected into a centrifuge tube. The cell suspensions are centrifuged at 1,500 rpm for 10 min at 4° C. The pellets are resuspended in 20 mM Tris-HCl buffer, pH 7.5, at 4° C., containing 250 mM sucrose, 1 mM MgCl$_2$, and 2 mM CaCl$_2$, by vortexing and 10 passes through a 25-gauge needle. The crude homogenate is further homogenized by a teflon-glass homogenizer, and is used as the cell homogenate. For the study of subcellular localization of 5α-reductase, the cell homogenate is centrifuged at 800×g for 10 min to yield a crude nuclear pellet. The resultant supernatant is centrifuged at 10,000×g for 15 min to produce a crude mitochondrial pellet. The supernatant is centrifuged at 100,000×g for 60 min to yield a microsomal pellet and cytosol. Each particulate fraction is washed twice and resuspended in the buffer.

A standard incubation mixture will consist of 50 nM [$^3$H]-testosterone, 1 mM NADPH, 100 mM sodium citrate, pH 5.5 or 100 mM Tris-HCl, pH 7.5, and 50 μl of the cell homogenate, in a final volume of 100 μl. Each tube contains 50–100 μg of cellular protein. Incubation is carded out at 37° C. for 30 min. During this incubation, the reaction is proportional to the time. For the study of optimum pH, citrate buffer is used at pH 4.5–6.5, and the Tris HCl buffer at pH 7.0–9.0. The protein content is determined by the method of Lowry, et. al., *Protein Measurement With The Folin Phenol Reagent* J. Biol. Chem. 193:265–275, 1951.

After incubation, the reaction is stopped by adding 4 times volume of chloroform-methanol (2/1:V/V) containing 110 μg each of carder steroids. The extracted steroids are analyzed by thin-layer chromatography as previously described by Gomez, et. al., *In Vitro Metabolism Of Testosterone-4-$^{14}$C and Δ-androstene-3, 17-dione-4-14C In Human Skin*. Biochem. 7:24–32, 1968, and the purity of each steroid is determined by the recrystallization method. The activity of 5α-reductase is expressed by the sum of dihydrotestosterone, androstanediol and androstanedione formed. [1,2-$^3$H]-testosterone (55.2 Ci/mmol) is obtainable from New England Nuclear Corporation (Boston, Mass.) and unlabeled steroids can be purchased from Sigma Chemical Company (St. Louis, Mo.). Fetal calf serum is obtainable from Hazleton (Lenaxa, Kans.). All other chemicals are of reagent grade.

Fuzzy Rat Acne Model

Adult fuzzy rats are a variety of rat that has stunted hair growth, brown colored seborrhea coveting their entire back skin and abnormally increased sebum production after puberty that has been demonstrataed to be due to circulating androgens. 0.1, 0.05 and 0.025% solutions of a selected 5α-reductase inhibitor of interest are prepared in a vehicle of propylene glycol, isopropanol, isopropyl myristate and water (50/30/2/18%), and is topically applied onto the backs of adult male fuzzy rats, 0.2 ml per animal daily for 4 weeks. Controls receive the vehicle alone and 5 of them are castrated. After 2 weeks seborrhea will be dose-dependently depleted and after 4 weeks bromodeoxyuridine (BrdU, 200 mg/kg) is intraperitoneally injected 2 hours before sacrifice. The skin tissues are incubated with EDTA (20 mM) in phosphate buffer, 1.5 hours at 37° C. The pilo-sebaceous unit attached to the epidermis is striped from the dermis and fixed with formalin for immuno-staining of BrdU. DNA synthesis cells showing a BrdU-positive nucleus are located in the outer glandular border. The number of S-phase cells per lobe is determined with a micro-image apparatus. Using formalin fixed skin, frozen serial sections are stained with 1% osmium and the size of the lobes is measured. A positive inhibitor of skin 5α-reductase will induce suppression of sebum production by inhibiting the rate of glandular cell turnover, and showing reduced lobular size.

The following describes an example methodology that can be used for detection of hair growth.

MACROPHOTOGRAPHY AND GLOBAL PHOTOGRAPHY PROCEDURE FOR DETECTION OF HAIR GROWTH

A. Macrophotographic Procedure

Location: ID card Haircount target area

Equipment: Film: Kodak-T-max 24 exposure each of same emulsion lot number

Camera: Nikon N-6000

Lens: Nikkor 60 mm f2.8

Flashes: Nikon SB-21B Macroflash

Device: registration device

Photographic Procedure:

In these clinical photographs, the only variable allowed is the haircount. Film emulsion, lighting, framing, exposure, and reproduction ratios are held constant.

1. The haircount area on the patient is prepared as follows: A small (~1 mm) dot tattoo is placed at the beginning of the study at the leading edge of the bald area directly interior to the center of the vertex bald spot, using a commercial tattooing machine or manually (needle and ink). An area approximately one square inch in size, centered at the tattoo at the leading edge of the balding area, is clipped short (~2 mm). Cut hairs are removed from the area to be photographed, using tape. Compressed air and/or ethanol wipes may also be used to facilitate removal of cut hairs.

2. Magnification: Each lens supplied has a fixed reproduction ratio of 1:1.2. Aperture: Every photograph is taken at f/22. Film: T-Max 100 (24 exposure) is used.

3. Patient's haircount target area. Three exposures (−⅔, 0, and +⅔ f-stop).

B. Global Photographic Procedure

Locations: Color card/patient Id Global photograph

Equipment: Film: Kodachrome KR-64 24 exposure each of same emulsion lot number

Camera: Nikon N-6000

Lens: Nikkor 60 mm f2.8

Flashes: Nikon SB-23

Color card/patient Id

Photographic Procedure

In these clinical photographs, the only variable allowed is the global area's appearance. Anything extraneous to the area (clothing, furniture, walls, etc.) is eliminated from the fields to be photographed.

1. Patients will have global photographs taken prior to hair clipping with the head in a fixed position (determined by the supplied stereotactic device). Hair on the patient's head is positioned consistently so as to not obscure the bald area.

2. Magnification: Each lens supplied has a fixed reproduction ratio of 1:6. Aperture: Every photograph will be taken at f/11. Film: Kodachrome (24 exposure) is used.

3. Patient's global photographs. Three exposures at zero compensation.

A trained technician places a transparency over the photograph and, using a felt tip pen, places a black dot over each visible hair. The dot map transparency is then counted using image analysis with computer assistance.

Photographs are coded with a random number corresponding to study site, visit number and patient allocation number to insure blinding to time. At Month 6, baseline and Month 6 photographs are counted and data analyzed for interim analysis. At Month 12, baseline, Month 6 and Month 12 photographs are counted and data analyzed for the primary endpoint.

Methodology for detection of hair growth is also described in Olsen, E. A. and Delong, E., *J. American Academy of Dermatology*, Vol. 23, p. 470 (1990).

While the invention has been described and illustrated with reference to certain particular embodiments thereof, those skilled in the art will appreciate that various changes, modifications and substitutions can be made therein without departing from the spirit and scope of the invention. For example, effective dosages other than the particular dosages as set forth herein above may be applicable as a consequence of variations in the responsiveness of the mammal being treated for any of the indications for the compounds of the invention indicated above. Likewise, the specific pharmacological responses observed may vary according to and depending upon the particular active compound selected or whether there are present pharmaceutical carriers, as well as the type of formulation and mode of administration employed, and such expected variations or differences in the results are contemplated in accordance with the objects and practices of the present invention. It is intended, therefore, that the invention be defined by the scope of the claims which follow and that such claims be interpreted as broadly as is reasonable.

What is claimed is:

1. A process for producing crystalline 4,7β-dimethyl-4-aza-5α-cholestan-3-one of structural formula (I)

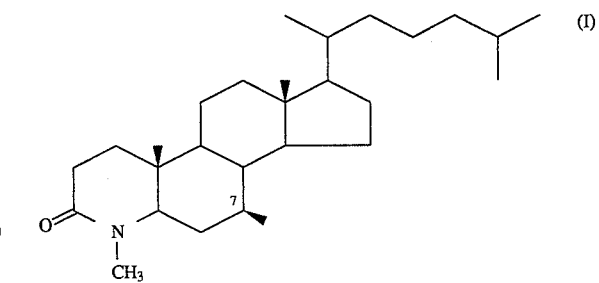

from 4,7β-dimethyl-4-aza-5α-cholestan-3-one oil comprising the steps of:

agitating 4,7β-dimethyl-4-aza-5α-cholestan-3-one oil at a temperature between −5° and 60° C. for a time sufficient of form crystals, and recovering the crystalline 4,7β-dimethyl-4-aza-5α-cholestan-3-one.

2. The process according to claim 1 comprising the steps of:

agitating 4,7β-dimethyl-4-aza-5α-cholestan-3-one oil at a temperature between −5° and 60° C. under an inert atmosphere, and recovering the crystalline 4,7β-dimethyl-4-aza-5α-cholestan-3-one.

3. The process according to claim 2 wherein the inert atmosphere is a nitrogen atmosphere.

4. The process according to claim 3 wherein the 4,7β-dimethyl-4-aza-5α-cholestan-3-one oil is agitated at a temperature between 40° and 55° C.

5. A process for producing crystalline 4,7β-dimethyl-4-aza-5α-cholestan-3-one of structural formula (I)

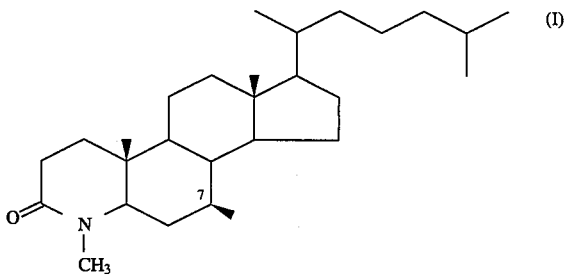

from 4,7β-dimethyl-4-aza-5α-cholestan-3-one oil comprising the steps of:

agitating 4,7β-dimethyl-4-aza-5α-cholestan-3-one oil containing residual solvent at a temperature between −5° and 60° C. for a time sufficient to form crystals to obtain crystalline 4,7β-dimethyl-4-aza-5α-cholestan-3-one of polymorphic Form I, and recovering the crystalline 4,7β-dimethyl-4-aza-5α-cholestan-3-one Form I.

6. The process according to claim 5 wherein the residual solvent is selected from heptane, tetrahydrofuran, acetone, acetic acid, methanol and toluene.

7. The process according to claim 6 wherein the residual solvent is toluene.

8. The process according to claim 6 wherein the 4,7β-dimethyl-4-aza-5α-cholestan-3-one oil is agitated at a temperature between 40° and 55° C.

9. The process according to claim 1 comprising the steps of:

agitating 4,7β-dimethyl-4-aza-5α-cholestan-3-one oil at a temperature between −5° and 60° C., seeding with crystalline 4,7β-dimethyl-4-aza-5α-cholestan-3-one, and recovering the crystalline 4,7β-dimethyl-4-aza-5α-cholestan-3-one.

10. The process according to claim 9 comprising the steps of:

agitating 4,7β-dimethyl-4-aza-5α-cholestan-3-one oil at a temperature between −5° and 60° C., seeding with 1 to 100 weight percent crystalline 4,7β-dimethyl-4-aza-5α-cholestan-3-one Form I, and recovering the crystalline 4,7β-dimethyl-4-aza-5β-cholestan-3-one Form I.

11. The process according to claim 9 comprising the steps of:

agitating 4,7β-dimethyl-4-aza-5α-cholestan-3-one oil at a temperature between −5° and 60° C., seeding with 5 to 10 weight percent crystalline 4,7β-dimethyl-4-aza-5α-cholestan-3-one Form I, and recovering the crystalline 4,7β-dimethyl-4-aza-5α-cholestan-3-one Form I.

12. The process according to claim 11 comprising the steps of:

agitating 4,7β-dimethyl-4-aza-5α-cholestan-3-one oil at a temperature between 45° and 60° C., seeding with 5 to 10 weight percent crystalline 4,7β-dimethyl-4-aza-5α-cholestan-3-one Form I, and recovering the crystalline 4,7β-dimethyl-4-aza-5α-cholestan-3-one Form I.

13. The process according to claim 1 which comprises the steps of:

agitating 4,7β-dimethyl-4-aza-5α-cholestan-3-one oil containing residual solvent at a temperature between −5° and 60° C., seeding with 10 weight percent crystalline 4,7β-dimethyl-4-aza-5α-cholestan-3-one Form I, and recovering the crystalline 4,7β-dimethyl-4-aza-5α-cholestan-3-one Form I.

14. The process according to claim 13 which comprises the steps of:

agitating 4,7β-dimethyl-4-aza-5α-cholestan-3-one oil containing residual solvent at a temperature between 40° and 55° C., seeding with 10 weight percent crystalline 4,7β-dimethyl-4-aza-5α-cholestan-3-one Form I, and recovering the crystalline 4,7β-dimethyl-4-aza-5α-cholestan-3-one Form I.

15. The process according to claim 1 which comprises the steps of:

agitating 4,7β-dimethyl-4-aza-cholestan-3-one oil at a temperature between −5° and 60° to obtain crystalline 4,7β-dimethyl-4-aza-cholestan-3-one of polymorphic Form I, wet milling the crystalline 4,7β-dimethyl-4-aza-cholestan-3-one of polymorphic Form I, and optionally formulating the milled crystalline 4,7β-dimethyl-4-aza-5α-cholestan-3-one of polymorphic Form I into a suitable pharmaceutical composition.

16. The process according to claim 15 wherein the 4,7β-dimethyl-4oaza-cholestan-3-one oil is agitated at a temperature between 45° and 55° C.

17. Crystalline 4,7β-dimethyl-4-aza-5α-cholestan-3-one of polymorphic Form I.

18. The crystalline material of claim 17 having the following x-ray powder diffraction pattern:

| Peak no. | Angle (deg.) | Tip width (deg.) | Peak intensity (cts.) | Back-ground (cts.) | D spacing (Ang) | I/Imax (%) | Sign |
|---|---|---|---|---|---|---|---|
| 1 | 2.855 | 0.72 | 10 | 7 | 30.9209 | 0.98 | 1.10 |
| 2 | 6.970 | 0.10 | 335 | 16 | 12.6721 | 31.9 | 6.03 |
| 3 | 9.510 | 0.21 | 77 | 18 | 9.2925 | 7.38 | 3.72 |
| 4 | 12.430 | 0.09 | 576 | 20 | 7.1153 | 54.87 | 2.00 |
| 5 | 12.750 | 0.07 | 262 | 20 | 6.9374 | 25.00 | 0.79 |
| 6 | 13.183 | 0.15 | 102 | 22 | 6.7108 | 9.72 | 0.85 |
| 7 | 13.680 | 0.18 | 196 | 24 | 6.4678 | 18.67 | 1.86 |
| 8 | 14.045 | 0.13 | 199 | 24 | 6.3006 | 18.94 | 4.27 |
| 9 | 15.2 | 0.16 | 1050 | 29 | 5.8243 | 100.0 | 15.49 |
| 10 | 16.228 | 0.06 | 894 | 32 | 5.4577 | 85.16 | 0.87 |
| 11 | 17.075 | 0.15 | 605 | 35 | 5.1867 | 57.65 | 0.98 |
| 12 | 17.430 | 0.10 | 930 | 36 | 5.0838 | 88.62 | 5.37 |
| 13 | 18.283 | 0.15 | 108 | 40 | 4.8487 | 10.30 | 1.17 |
| 14 | 19.167 | 0.09 | 445 | 44 | 4.6267 | 42.41 | 1.78 |
| 15 | 20.140 | 0.15 | 543 | 46 | 4.4055 | 51.72 | 8.13 |
| 16 | 21.030 | 0.36 | 42 | 49 | 4.2210 | 4.02 | 0.91 |

-continued

| Peak no. | Angle (deg.) | Tip width (deg.) | Peak intensity (cts.) | Background (cts.) | D spacing (Ang) | I/Imax (%) | Sign |
|---|---|---|---|---|---|---|---|
| 17 | 22.300 | 0.09 | 339 | 53 | 3.9834 | 32.25 | 1.17 |
| 18 | 23.083 | 0.24 | 156 | 58 | 3.8501 | 14.88 | 0.78 |
| 19 | 24.153 | 0.12 | 216 | 61 | 3.6819 | 20.58 | 1.12 |
| 20 | 24.725 | 0.36 | 128 | 62 | 3.5983 | 12.16 | 3.89 |
| 21 | 25.613 | 0.36 | 303 | 66 | 3.4752 | 28.84 | 11.22 |
| 22 | 26.253 | 0.21 | 154 | 67 | 3.3919 | 14.65 | 1.93 |
| 23 | 28.225 | 0.30 | 98 | 66 | 3.1592 | 9.34 | 2.04 |
| 24 | 28.910 | 0.21 | 106 | 66 | 3.0859 | 10.11 | 1.82 |
| 25 | 29.823 | 0.15 | 40 | 79 | 2.9935 | 3.78 | 0.95 |
| 26 | 30.488 | 0.36 | 29 | 79 | 2.9297 | 2.78 | 0.76 |
| 27 | 31.465 | 0.42 | 38 | 86 | 2.8409 | 3.66 | 3.98 |
| 28 | 32.785 | 0.24 | 88 | 76 | 2.7295 | 8.42 | 1.62 |
| 29 | 33.495 | 0.30 | 56 | 61 | 2.6732 | 5.36 | 0.93 |
| 30 | 35.445 | 0.42 | 45 | 94 | 2.5305 | 4.28 | 2.57 |
| 31 | 36.325 | 0.42 | 45 | 94 | 2.5305 | 4.28 | 2.57 |
| 32 | 37.435 | 0.42 | 132 | 104 | 2.4004 | 12.6 | 4.07 |
| 33 | 36.398 | 0.09 | 92 | 112 | 2.3424 | 9.34 | 0.78 |

19. Crystalline 4,7β-dimethyl-4-aza-5α-cholestan-3-one of polymorphic Form I prepared according to the process of claim 1.

20. Crystalline 4,7β-dimethyl-4-aza-5α-cholestan-3-one of polymorphic Form II.

21. The crystalline material of claim 20 having the following X-ray powder diffraction pattern:

| Peak no. | Angle (deg.) | Tip width (deg.) | Peak intensity (cts.) | Background (cts.) | D spacing (Ang) | I/Imax (%) | Sign |
|---|---|---|---|---|---|---|---|
| 1 | 3.025 | 0.07 | 424 | 48 | 29.1835 | 87.68 | 1.48 |
| 2 | 3.093 | 0.06 | 317 | 48 | 28.5467 | 65.46 | 1.48 |
| 3 | 5.8825 | 0.15 | 46 | 28 | 15.0121 | 12.57 | 3.31 |
| 4 | 8.4975 | 0.15 | 46 | 28 | 10.3973 | 9.55 | 0.83 |
| 5 | 10.293 | 0.24 | 45 | 40 | 8.5877 | 9.27 | 0.98 |
| 6 | 12.840 | 0.12 | 292 | 55 | 6.8890 | 60.42 | 0.78 |
| 7 | 14.943 | 0.15 | 350 | 135 | 5.9241 | 72.25 | 0.79 |
| 8 | 16.080 | 0.04 | 243 | 137 | 5.5075 | 50.28 | 0.87 |
| 9 | 16.465 | 0.24 | 339 | 142 | 5.3796 | 69.95 | 2.00 |
| 10 | 17.953 | 0.21 | 484 | 154 | 4.9370 | 100.00 | 2.69 |
| 11 | 18.193 | 0.12 | 342 | 159 | 4.8724 | 70.71 | 0.78 |
| 12 | 22.665 | 0.48 | 53 | 149 | 3.920 | 11.01 | 1.35 |
| 13 | 24.568 | 0.30 | 55 | 139 | 3.6206 | 11.31 | 1.02 |
| 14 | 29.573 | 0.96 | 38 | 106 | 3.0183 | 7.94 | 1.45 |

22. A pharmaceutical composition consisting essentially of 0.1 to 1,000 milligrams of crystalline 4,7β-dimethyl-4-aza-5α-cholestan-3-one of polymorphic Form I according to claim 17 and a pharmaceutically acceptable carrier.

23. The composition of claim 22 wherein the pharmaceutical composition is adapted for topical administration.

* * * * *

UNITED STATES PATENT AND TRADEMARK OFFICE
CERTIFICATE OF CORRECTION

PATENT NO. : 5,585,383

DATED : 12/17/96

INVENTOR(S) : ANDREW L. FORMAN et al.

It is certified that error appears in the above-identified patent and that said Letters Patent is hereby corrected as shown below:

Col. 31, lines 59 & 60, should read --recovering the crystalline 4,7 β-dimethyl-4-aza-5α-cholestan-3-one Form I.--

Col. 32, lines 43&44, should read -- dimethyl-4-aza-cholestan-3-one oil is agitated at a temperature between 45° and 55° C. --

Signed and Sealed this

Twentieth Day of May, 1997

Attest:

BRUCE LEHMAN

*Attesting Officer*   *Commissioner of Patents and Trademarks*